US009510933B2

(12) United States Patent
Ingham et al.

(10) Patent No.: US 9,510,933 B2
(45) Date of Patent: Dec. 6, 2016

(54) ACELLULAR VASCULAR PRODUCTS

(75) Inventors: Eileen Ingham, Leeds (GB); John Fisher, Leeds (GB); Stacy-Paul Wilshaw, Leeds (GB)

(73) Assignee: Tissue Regenix Limited, York (GB)

( * ) Notice: Subject to any disclaimer, the term of this patent is extended or adjusted under 35 U.S.C. 154(b) by 590 days.

(21) Appl. No.: 13/876,429

(22) PCT Filed: Sep. 26, 2011

(86) PCT No.: PCT/GB2011/051817
§ 371 (c)(1),
(2), (4) Date: Mar. 27, 2013

(87) PCT Pub. No.: WO2012/042250
PCT Pub. Date: Apr. 5, 2012

(65) Prior Publication Data
US 2013/0197667 A1    Aug. 1, 2013

(30) Foreign Application Priority Data

Sep. 27, 2010  (GB) .................................. 1016150.3
Dec. 9, 2010   (GB) .................................. 1020846.0

(51) Int. Cl.
*A61F 2/02*   (2006.01)
*A61F 2/06*   (2013.01)
*A61L 27/36*  (2006.01)
*A61L 27/50*  (2006.01)

(52) U.S. Cl.
CPC .............. *A61F 2/06* (2013.01); *A61L 27/3625* (2013.01); *A61L 27/3695* (2013.01); *A61L 27/507* (2013.01); *A61L 2430/40* (2013.01)

(58) Field of Classification Search
CPC ....................................................... A61F 2/06
USPC ........................................ 623/23.72; 435/1.1
See application file for complete search history.

(56) References Cited

U.S. PATENT DOCUMENTS

| 4,776,853 A | 10/1988 | Klement et al. |
| 8,735,054 B1 * | 5/2014 | Sun ................................ 435/1.1 |
| 2004/0208842 A1 * | 10/2004 | Ritchie ................... A61K 8/41 424/70.21 |
| 2005/0266390 A1 * | 12/2005 | Ueda ....................... A61F 2/062 435/1.1 |
| 2008/0306610 A1 * | 12/2008 | Wang ..................... A61K 35/32 623/23.72 |
| 2013/0028981 A1 * | 1/2013 | Gratzer ............... A61L 27/3641 424/548 |

FOREIGN PATENT DOCUMENTS

| CN | 101184775 | 5/2008 |
| CN | 101474426 | 7/2009 |
| CN | 101573148 | 11/2009 |
| GB | 2375771 A | 11/2002 |
| GB | 2443938 A | 5/2008 |
| WO | WO 02/096476 A1 | 12/2002 |
| WO | WO 2004/003178 A2 | 1/2004 |

OTHER PUBLICATIONS

Brockbank, Kelvin et al. Tissue Preservation. Advances in biopreservation. Jun. 15, 2006. pp. 157-195.*
Brockbank (Tissue Preservation, 2006).*
International Search Report corresponding to PCT/GB2011/051817 mailed Mar. 20, 2012.
Written Opinion of the International Preliminary Examining Authority corresponding to PCT/GB2011/051817 mailed Mar. 20, 2012.
International Preliminary Report on Patentability and Written Opinion Corresponding to International Application No. PCT/GB2011/051817 ; Date of Mailing: Apr. 11, 2013; 10 Pages.

* cited by examiner

*Primary Examiner* — Scott Long
*Assistant Examiner* — Nghi Nguyen
(74) *Attorney, Agent, or Firm* — Myers Bigel, P.A.

(57) ABSTRACT

A product comprising a natural acellular xenogenic vascular tissue matrix having at least an 80% reduction in DNA content as compared to an untreated control vascular tissue matrix and being antigenically inert by being substantially free of epitopes capable of reacting with pre-formed human antibodies and also without having the ability to substantially activate complement. The invention also includes methods of preparing such products and uses of the products especially in bypass surgery.

12 Claims, 11 Drawing Sheets

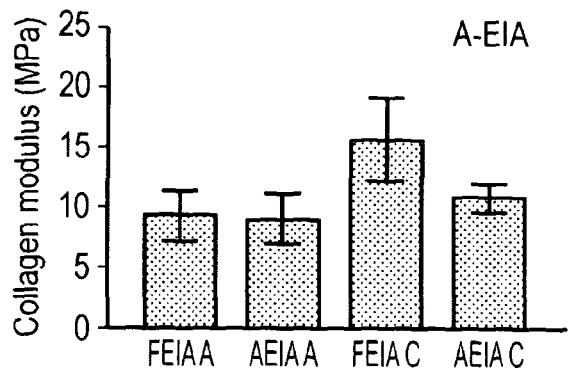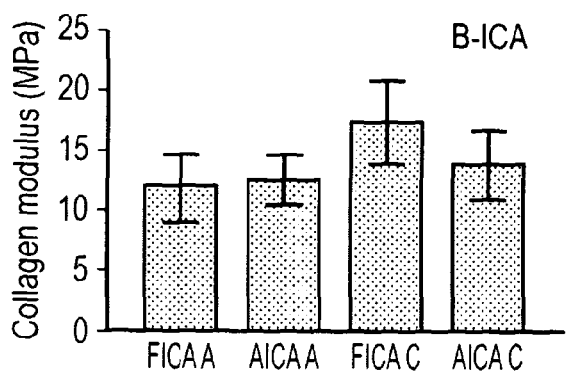
FIG. 17A   FIG. 17B
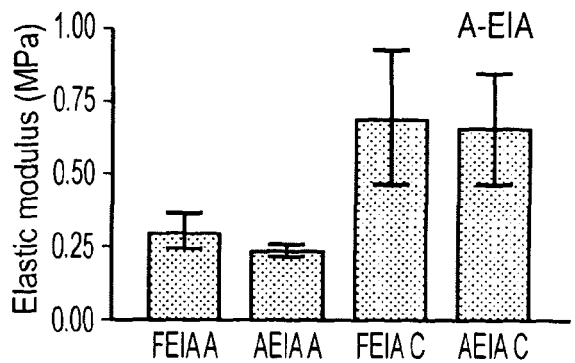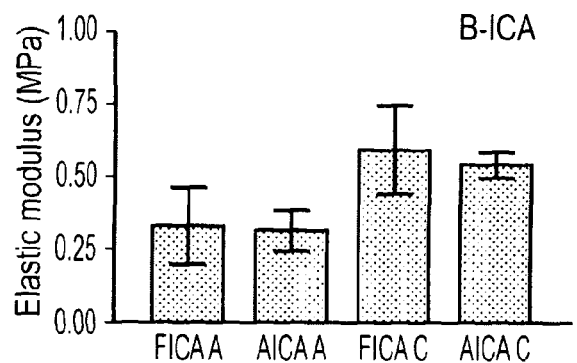
FIG. 18A   FIG. 18B
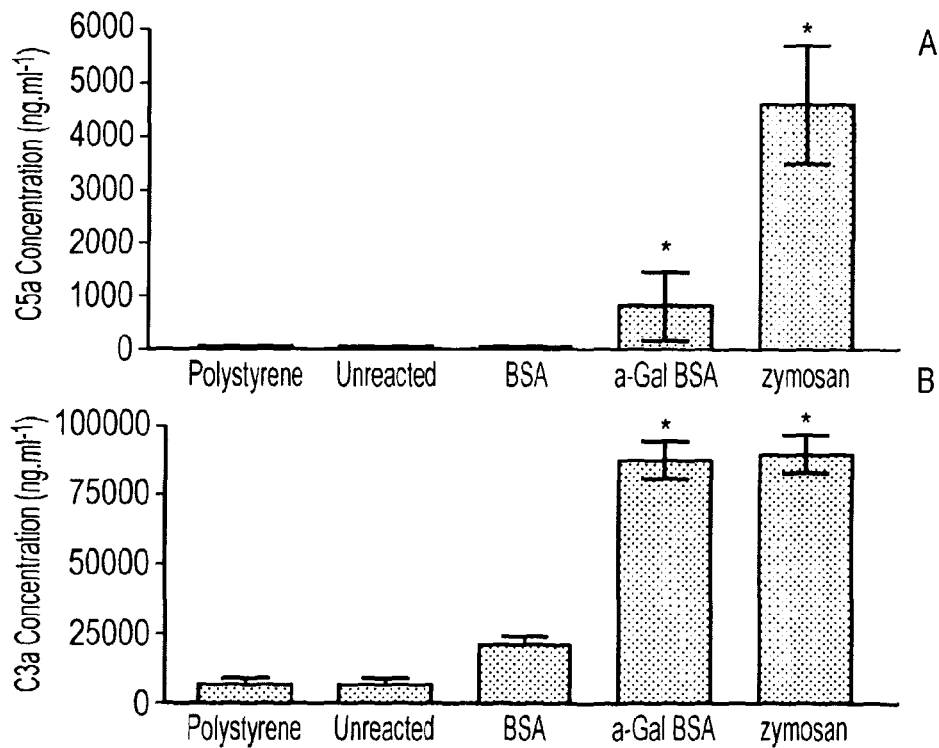
FIG. 19

ACELLULAR VASCULAR PRODUCTS

STATEMENT OF PRIORITY

This application is a 35 U.S.C. §371 national phase application of PCT International Application No. PCT/GB2011/051817, having an international filing date of Sep. 26, 2011, which claims priority to British Patent Application No. 1016150.3, filed Sep. 27, 2010 and British Patent Application No. 1020846.0, filed Dec. 9, 2010. The disclosures of each of these applications are incorporated herein by reference in their entireties.

This invention relates to acellular xenogeneic matrices and in particular to small and medium diameter vascular products such as acellular arteries that are physically compatible and non-immunogenic. The invention includes inter alia uses of the acellular products particularly in vascular bypass surgery and methods of making the acellular vascular matrices.

BACKGROUND

Complement activation is a potent mediator and diagnostic indicator of inflammation and rejection in solid organ transplants. Mechanistically, a series of effector molecules in the complement cascade mediate pro-inflammatory functions that can account for chemotaxis and activation of cells of the innate immune system, such as granulocytes and monocytes. Simultaneously, many of these same complement mediators activate and disrupt the endothelial cell interface between the recipient and the transplant, in addition, complement can stimulate B and T lymphocytes of the adaptive immune system. Complement also participates in the non-inflammatory clearance of apoptotic cells. Therefore, the complement cascade can be activated by multiple mechanisms and various components of complement can modulate the response to transplants in different directions.

To date no xenotransplantation trials have been entirely successful due to the many obstacles arising from the response of the recipient's immune system. This response, which is generally more extreme than in allotransplantations, ultimately results in rejection of the xenograft. There are several types of xenograft rejection: hyperacute rejection and acute vascular rejection which are due to the response of the humoral immune system and cellular rejection and chronic rejection which is based on cellular immunity.

Hyperacute rejection is mediated by the binding of xenoreactive natural antibodies (XNAs) to the donor endothelium causing activation of the human complement system, the major epitope XNAs target is the α-gal epitope (galα1-3galβ1-(3)4glcnac-r) which is abundantly present on glycolipids and glycoproteins of non-primate mammals and new world monkeys due to glycosylation by the enzyme α1,3galactosyltransferase (α1,3gt). In humans, apes and old world monkeys, this epitope is absent because the α1,3gt gene was inactivated in ancestral old world primates. Instead, humans, apes and old world monkeys produce the anti-gal antibody, which specifically interacts with α-gal epitopes and which constitutes ~1% of circulating immunoglobulins. The immune response due to α-gal epitopes is an important factor in xenogenic organ/tissue transplant failure. The elimination of the interaction between the natural anti-gal antibodies and α-gal epitopes on the xenografts is a prerequisite to the success of xenografts in humans. Anti-gal has functioned as an immunological barrier, preventing the transplantation of pig organs into humans, because anti-gal binds to the α-gal epitopes expressed on pig cells. It is known from the prior art to generate α1,3gt knockout pigs that lack α-gal epitopes which has resulted in a partial elimination of this immunological barrier and hence partially overcome hyperacute rejection, however transgenic production of pigs is both expensive and time consuming. Moreover, a low but potentially significant levels of galα(1,3)gal are still expressed on the tissues of α1,3gt knockout animals, which indicates that another glycosyltransferase is involved in the synthesis of this epitope (Milland et al Immunol. Cell Biol 2005, 83, 687-693). It is also known from the prior art that green coffee bean α-galactosidase and recombinant human α-galactosidase can remove α-gal epitopes from the cell surface of tissues such as the porcine aortic valve and pericardial tissue, but enzymatic treatments have limitations not only on cost effectiveness but can also affect the histoarchitecture of the tissue and leave undesirable enzymatic residues. In order to overcome hyperacute rejection it is also known to inhibit the recipient's complement cascade through the use of cobra venom factor (which depletes C3), soluble complement receptor type 1, anti-C5 antibodies, or C1 inhibitor (C1-INH). Disadvantages of this approach include the toxicity of cobra venom factor, and most importantly these treatments would deprive the individual of a functional complement system. As regards acute vascular rejection, this type of rejection occurs in discordant xenografts within 2 to 3 days, if hyperacute rejection is prevented. The process is much more complex than hyperacute rejection and is currently not completely understood however, if hyperacute and acute vascular rejection are avoided accommodation is possible, which is the survival of the xenograft despite the presence of circulating XNAs. The graft is given a break from humoral rejection when the complement cascade is interrupted, circulating antibodies are removed, or their function is changed, or there is a change in the expression of surface antigens on the graft. This allows the xenograft to up-regulate and eventually express protective genes.

It is therefore desirable that acellular xenogeneic vascular matrices do not activate complement. It is also desirable that acellular xenogeneic vascular matrices are devoid of antigenic components and especially α-gal epitopes in order to mitigate antibody-mediated inflammatory reactions. It is also desirable to provide an alternative and more cost effective method of preparing small and medium diameter vascular products for bypass surgery. It is also desirable to provide acellular xenogeneic vascular matrices for transplantation that are devoid of residual α-galactosidase enzymatic residues.

BRIEF SUMMARY OF THE DISCLOSURE

According to a first aspect of the present inventions there is provided a product comprising a natural acellular xenogenic vascular tissue matrix having at least an 80% reduction in DNA content as compared to an untreated control vascular tissue matrix, the product being substantially free of epitopes capable of reacting with pre-formed human antibodies and also without the ability to substantially activate complement.

Reference herein to "without the ability to substantially activate complement" indicates that the product of the invention has about the same level of complement activation as fresh human femoral arteries in a complement activation assay.

Preferably, the acellular xenogenic vascular tissue is substantially free from α-gal epitopes.

Reference herein to "substantially free of epitopes capable of reacting with pre-formed human antibodies" indicates that the product of the present invention has about the same level of α-gal epitopes as fresh or acellular human femoral arteries Preferably, the acellular xenogenic vascular tissue matrix may have a reduction in DNA content as compared to a control untreated or natural vascular tissue matrix at least 80% or more that is to say it may have a reduction of any integer greater than 80% and maximally 100%.

Preferably, the vascular tissue is porcine or bovine in origin. Preferably the porcine derived vascular tissue is a small or medium diameter blood vessel and more preferably is either a porcine external iliac artery (EIA) or a porcine internal carotid artery (ICA).

It will be appreciated that the vascular tissue may also be derived from other mammalian species such as and without limitation, ovine or llama, large avian species (e.g. ostrich) and large marsupial species (e.g. kangaroo).

It will be appreciated that the vascular tissue may also be large diameter blood vessel for example porcine or bovine aorta.

Reference herein to "small diameter" blood vessels is an accepted term in the art and refers to blood vessels with an inner or internal diameter of less than 6 mm whereas "medium diameter" refers to blood vessels having an inner or internal diameter of between 6 to 15 mm and "large diameter" refers to blood vessels having an inner or internal diameter of around 25 mm.

In the embodiments of the invention where the acellular xenogenic vascular tissue matrix is bovine derived, the vascular tissue is selected from the group comprising carotid artery, internal mammary artery, internal thoracic artery, mesenteric vein and jugular vein.

Preferably, the acellular xenogenic vascular tissue has an equivalent or not substantially different collagen, glycosaminoglycan and elastin content as compared to fresh or untreated tissue.

Typical collagen levels of fresh untreated ICA tissue are in the range of 400-1000 μg/mg and more preferably in the range of 600-800 μg/mg and for EIA are in the range 200-1000 μg/mg and more preferably in the range of 450-650 μg/mg. Typically, the glycosaminoglycan levels of fresh untreated ICA and EIA tissues are in the range of 25-200 μg/mg and more preferably in the range of 50-100 μg/mg.

Preferably, the acellular xenogenic vascular tissue has an equivalent or not significantly different value for burst pressure, suture retention, ultimate tensile strength, dilatation and low strain rate failure values as compared to fresh or untreated tissue.

Typically the mean burst pressure of fresh untreated ICA and EIA tissue is above 3000 mmHg, typically the suture retention of fresh untreated ICA and EIA tissue is in the range 1-5 N, typically the low strain rate failure of fresh untreated ICA and EIA is the axial direction is in the range 2.5 to 6.5 MPa and more preferably is in the range 3.5 to 5.5 MPa and in the circumferential direction is in the range 1 to 6 MPa and more preferably is in the range 2 to 5 MPa, typically the mean ultimate tensile strength of fresh untreated ICA and EIA tissue is in the range of 3 to 5 MPa.

Preferably, a typical length of porcine derived acellular xenogenic vascular tissue is up to around 30 cm and up to around 80 cm for bovine derived tissue.

The acellular xenogenic vascular tissue of the present invention is a natural scaffold, that is to say it is not genetically altered and is substantially free from any α-galactosidase enzyme residues. Moreover, it advantageously has approximately the same biochemical and mechanical properties as fresh or untreated tissue so that it performs as a fresh or untreated tissue whilst being effectively antigenically inert. Accordingly it is an ideal product candidate for transplantation and by pass replacement surgery.

Preferably, the acellular xenogenic vascular tissue further comprises a coating, the coating being provided by a suitable material coated onto either or both of an internal surface (lumen) or external surface thereof. This embodiment of the invention is of particular utility for vascular grafts.

Preferably, the coating material is selected to improve vessel patency, or to aid/restore either the vessel lumen or the endothelial lining on the inside surface of the vessel lumen.

Preferably, the coating is a luminal coating and the coating material is selected from the group comprising: anticoagulants such as heparin, synthetic pentasaccharide inhibitors, direct thrombin inhibitors, Vitamin K antagonists, Factor Xa inhibitors, silver, collagen IV, elastin, glycoproteins such as laminin or fibronectin, glycosaminoglycans such as hyaluronan, chondroitin sulphate and synthetic or natural peptides or mixtures thereof Preferably, the acellular xenogenic vascular tissue may be seeded with a single or mixed population of cells seeded thereon or therein, the cell population being selected according to a transplant site and being selected from the group comprising epithelial cells such as endothelial, mesothelial or smooth muscle cells, FIBROBLASTS, pluripotent and multipotent stem cells such as autologous and allogenic adult stem cells, haematopoietic, mesenchymal, neuronal, endothelial and embryonic stem cells.

According to a further aspect of the invention there is provided a method of preparing a natural acellular xenogenic vascular tissue the method comprising, obtaining a suitable replacement blood vessel and subjecting it to the following methodological steps:
  (i) an incubation with EDTA;
  (ii) a first disinfection wash;
  (iii) at least two cycles of an incubation with a hypotonic buffer and an anionic detergent;
  (iv) a nuclease treatment;
  (v) a hypertonic wash; and
  (vi) a terminal sterilization process.

Preferably, steps (i) and (ii) may be performed in a reverse order, indeed the steps of the present invention are not restricted to the order as given above and are not intended to limit the scope of the invention.

Preferably, the incubation with EDTA is performed in a hypertonic buffer solution such as for example a 50 mM TRIS, 1.5 M NaCl and a typical protocol will be 200 mM EDTA in such a hypertonic buffer at around 4° C. for at least 24 hours. The hypertonic solution has a an approximately physiological pH that is very mildly alkaline and is approximately at a pH of between 7.2 to 7.4.

Preferably, the first disinfectant wash of step (ii) comprises a wash in a hypotonic buffer solution comprising vancomycin, gentamicin and polymyxin, a suitable wash period is around 30 min at a temperature of around 37° C.

Preferably the hypotonic incubation step of step (iii) comprises a first incubation with a hypotonic buffer typically comprising 10 mM TRIS and subsequently with a hypotonic buffer additionally comprising 2.7 mM EDTA, 10 KIU/ml aprotinin. Incubation conditions are typically for between 24 to 56 hours at around 4° C. For a further incubation, the hypotonic buffer additionally comprises an anioinic detergent such as SDS at around a concentration 0.1% (w/v), during this part of the incubation the temperature is about 37° C. This cycle of incubations can be repeated one or more times.

Preferably, the tissue may then be repeatedly washed in Dulbecco's phosphate buffered saline prior to subjecting the tissue to the nuclease treatment of step (iv). The nuclease treatment typically comprises an incubation for about 3 hr at 37° C. in a nuclease solution comprising 50 mM TRIS, 50 U/ml DNAase and 1 U/ml RNAase. The tissue is then washed repeatedly prior to step (v).

Preferably, the hypertonic incubation of step (v) comprises a incubation for about 24 hr at 37° C. in 50 mM TRIS, 1.5 M NaCl. The tissue is then repeatedly washed prior to step (vi).

Preferably, the terminal sterilization process provides viral clearance and a reduction of bioburden for the acellular xenogenic vascular tissue prior to storage or transplantation into a recipient.

The terminal sterilization step may ideally be performed by any one or more of the following processes, for example: incorporation or coating of antimicrobial agents such as antibiotics, defensins and metals such as $Ag^{2+}$; treatment with a cross-linking agent such as glutaraldehyde, carbodiimides; treatment with sterilizing agents such as peracetic acid, ethylene oxide, propylene oxide and sodium hydroxide, irradiation with for example γ or e-beams and treatment with supercritical $CO_2$.

The sterilization step may, for example, be a second disinfection wash comprises of step comprising an incubation with peracetic acid at a concentration of about 0.1% v/v for about 4 hr at 37° C. The tissue may then be further washed with a suitable terminal cleaning solution such as Dulbecco's phosphate buffered saline.

The concentrations and incubation conditions are not intended to limit the scope of the application but merely to provide exemplary methodological conditions.

Preferably, the method further includes the step of coating an internal and/or external surface either of the natural acellular xenogenic vascular tissue with a coating agent as herein before described.

Preferably, the method further includes the step of seeding the natural acellular xenogenic vascular tissue with a single or mixed population of cells as herein before described.

Vascular tissues such as arteries are effectively tubular and so it is very difficult to ensure that the internal surfaces of the arterial lumen are sufficiently treated to remove epitopes capable of reacting with pre-formed human antibodies and epitopes capable of activating complement. In one embodiment of the invention, the vascular tissue may be perfused with continually moving fluid media. In addition or alternatively, the vascular tissue may also be distended during the preparation and incubation steps so as to thin the walls of the vascular tissue to encourage penetration of the various fluids. The inventors have demonstrated that the methodology of the present invention results in successful treatment even for internal surfaces.

According to a yet further aspect of the invention there is provided a product comprising a natural acellular xenogenic vascular tissue matrix tissue product obtainable by the methods of the invention for use as a transplant tissue Preferably, the transplant tissue product is for use in bypass surgery and especially coronary and limb bypass surgery it is also for use vascular access for example AV access.

Embodiments of the invention using bovine derived vascular tissue are of particular utility in limb bypass surgery and as vascular access means because of the length of the vascular material being in the range of up to 80 cm in length.

According to a yet further aspect of the invention there is provided a method of vascular bypass surgery comprising replacing a damaged or blocked blood vessel with a natural acellular xenogenic vascular tissue matrix tissue product of the first aspect of the invention or as prepared by the methods of the present invention.

BRIEF DESCRIPTION OF THE DRAWINGS

Embodiments of the invention are further described hereinafter with reference to the accompanying drawings, in which:

FIGS. 5 A, B, E and F are labelled with crude antibody, Figures C and G with 0.39 mg·ml$^{-1}$ purified antibody and Figures D and H with 0.16 mg·ml$^{-1}$ of pure antibody.

FIG. 17 shows circumferential and axial collagen phase slope of fresh and acellular porcine EIA (A) and ICA (B). Data is expressed as mean (n=6)±95% confidence limits.

FIG. 18 shows circumferential and axial elastin phase slope of fresh and acellular porcine EIA (A) and ICA (B). Data is expressed as mean (n=6)±95% confidence limits.

FIG. 19 shows ELISA for detection of (a) C3a or (b) C5a following reaction of normal human serum with tissue culture plastic, PBS, BSA, α-Gal BSA or Zymosan. Data is expressed as mean (n=6)±95% confidence limits, * represents a significant difference [compared to polystyrene] as determined by one-way ANOVA and post hoc T test.

DETAILED DESCRIPTION

Figure 1:
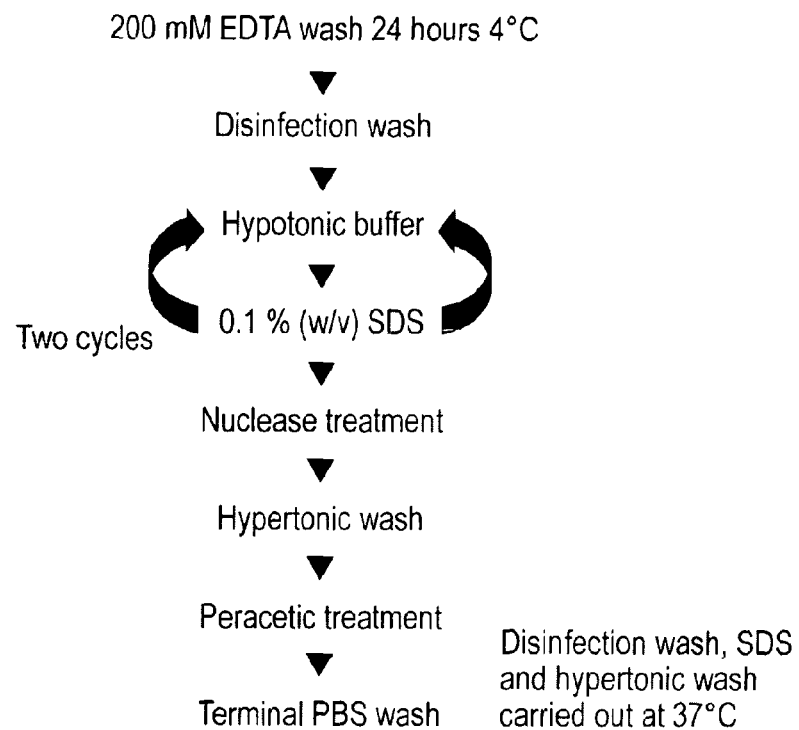
FIG. 1 shows a flow diagram of the decellularisation protocol to produce acellular tissue.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The present invention provides acellular products and methods of producing them. Two particularly suitable vessels were identified, porcine external iliac and internal carotid arteries and initial studies established a protocol capable of removing all cells and >80% DNA from the vessels, this was based on using two cycles of hypotonic buffer at 4° C. and 1 mg·ml$^{-1}$ SDS solution at 37° C. respectively. Vessels decellularised using a single cycle of hypotonic buffer and SDS solution demonstrated the presence of residual cells and cellular remnants when stained using haematoxylin and eosin and DAPI. Therefore two cycles of hypotonic buffer and SDS was chosen as the optimal decellularisation process as this was capable of reliably producing acellular vessels.

Antibody labelling using a monoclonal antibody against the α-Gal epitope demonstrated it to be present within acellular external iliac arteries and internal carotid arteries. Antibody labelling was carried out using cryoembedded tissue samples, zinc fixed paraffin wax embedded samples and formalin fixed paraffin wax embedded samples. Commercially there is only a single antibody clone from a single source; this is supplied as a crude preparation. The crude preparation consistently produced high background staining compared to the IgM negative control antibody. The antibody was purified using an IgM binding column. The antibody was then dialysed and concentrated using centrifugal filter devices. Labelling using the purified antibody demonstrated significantly reduced levels of background compared to the crude preparation. Cryoembedded samples produced the most sensitive labelling and formalin fixed samples the weakest labelling. Therefore zinc fixed paraffin embedded samples were used as a standard technique as this produced superior histology compared to cryoembedded samples and an increased sensitivity over formalin fixed samples. The levels of α-Gal throughout the matrix were substantially lower when compared to fresh control tissues. However the epitope was detectable. Attempts were made to remove the α-Gal epitope by using increasing cycles of hypotonic buffer and SDS solution. Monoclonal antibody labelling demonstrated there to be no substantial reduction in α-Gal levels when two cycles was used compared to a single cycle.

The two cycle hypotonic buffer and SDS solution failed to remove α-Gal from the acellular matrices. It was hypothesised that an initial step to remove the endothelial cells from the surface of the vessel lumen would reduce the amount of α-Gal within the acellular matrices. To this end Versene and various concentrations of EDTA were used prior to the decellularisation process in order to chelate any metal ions to aid in release of the endothelial cells from the lumen of the vessel. Pre-treatment using 200 mM EDTA at 4° C. for 25 hours proved successful in reducing the levels of α-Gal with acellular vessels, this was incorporated into the decellularisation process of the present invention.

Hypertonic buffer (10 mM Tris, 1.5 M sodium chloride pH 7.4) treatment following decellularisation has been used during the decellularisation process to further reduce the levels of α-Gal present within acellular cardiovascular tissues. Further antibody labelling demonstrated a single cycle of hypertonic buffer at 37° C. for 24 hours in combination with pre-treatment using 200 mM EDTA at 4° C. for 24 hours with agitation was successful in reducing the levels of α-Gal with the acellular vessels. It also showed that there was no obvious improvement in the reduction of α-Gal with increasing cycles (up to three) of hypertonic buffer treatment at 37° C.

In order to determine if there was residual α-Gal within the acellular matrices it was fundamental that the specificity of the antibody be determined. This was accomplished by adsorbing the purified antibody using α-Gal BSA. BSA was also included as a control. Following adsorption the α-Gal antibody would have bound to the α-Gal BSA and thus ablating its ability to bind to any α-Gal epitopes within the tissue being labelled. Therefore any staining using this could be regarded as background. Adsorption using BSA alone demonstrated that protein:protein interactions would not affect the ability of the antibody to detect α-Gal epitope. Comparison of the data obtained using the antibody absorbed with BSA and the antibody absorbed with α-Gal BSA with the decellularised tissues and the decellularised tissues treated with α-galactosidase indicated that: Acellular EIA appeared to have residual α-Gal which could be further reduced by the use of the enzyme. This staining was in the matrix and not on the intimal surface. The acellular ICA had some very weak staining that could not be removed by the use of α-galactosidase. The data overall indicated that there was minimal α-Gal in the acellular vessels.

The antibody adsorption assay utilised the same monoclonal antibody. The advantage of this assay is that a much larger volume of material can be assayed compared to immunocytochemistry which is limited to very thin sections. In addition, the antibody adsorption assay gave a semi-quantitative assessment of the levels of α-Gal present in the different tissue samples. Samples of fresh vessels demonstrated the highest levels of α-Gal expression. Fresh porcine EIA and ICA treated with α-galactosidase was shown to be devoid of α-Gal (not different to the no tissue control) indicating that the assay was successful. Samples of acellular EIA and ICA demonstrated levels of α-Gal that were not significantly different to fresh and acellular human common femoral artery as well as the no tissue control.

Histological evaluation demonstrated the matrix architecture and composition of the acellular samples to be similar to fresh controls. The acellular matrices showed a more relaxed open structure when compared to fresh porcine vessels. There did not appear to be any qualitative differences in the GAG, collagen, or elastin content of acellular EIA or ICA compared to fresh vessels. Results of the hydroxyproline, denatured collagen and glycosaminoglycan assays indicated that the decellularisation process did not lead to loss of collagen or glycosaminoglycans from the tissue. Whilst quantitative biochemical analysis provided information on the collagen and glycosaminoglycan content of the acellular matrix, it was limited in that it was not possible to assess the structural integrity of the components. The levels of denatured collagen were therefore determined following α-chymotrypsin treatment, which is able to digest degraded collagen without affecting native collagen (Bank et al., 1997). Following digestion, the tissue supernatant (containing any degraded collagen) was assayed for the presence of hydroxyproline. Results indicated that there was no significant increase in the total amount of denatured collagen present in acellular EIA or ICA compared to fresh vessels.

Concerns regarding the presence of residual SDS were addressed through quantification of the SDS concentration within each of the decellularisation solutions used to produce acellular EIA and ICA. The use of radiolabelled SDS ($C^{14}$) demonstrated there to be extremely low levels of SDS present within the final wash solutions used in the decellularisation process.

Biocompatibility of the acellular matrices was demonstrated using the extract and contact cytotoxicity assays. Each assay used two different cell lines, baby hamster kidney cells, and mouse 3T3 cells. Previous data has demonstrated the in vivo biocompatibility of SDS treated matrices and it was not necessary to repeat this using acellular EIA or ICA.

DNA quantification using a number of different assays indicated there to be a greater than 90% reduction in DNA levels following decellularisation and these values were significantly lower than the amount of DNA isolated from Surgisis. The levels of DNA isolated from acellular porcine EIA and ICA were comparable to those of Permacol and CollaMend. Acellular EIA and ICA contained 0.014 $\mu g \cdot mg^{-1}$ and 0.019 $\mu g \cdot mg^{-1}$ respectively of DNA. Surgisis contained 0.119 $\mu g \cdot mg^{-1}$, Permacol 0.028 $\mu g \cdot mg^{-1}$ and CollaMend 0.017 $\mu g \cdot mg^{-1}$ of DNA. PCR demonstrated any residual DNA was either small fragmented pieces of DNA that could not be amplified or non-coding 'junk' DNA. The presence of porcine endogenous retroviruses is a concern for any porcine derived xenogeneic graft. Despite this there is virtually no information regarding the effects of such viruses on humans, the potential for transmission or minimum safe levels. PERV copy number was determined using quantitative PCR using a Taqman probe. The data indicated PERV DNA to be present in all samples of acellular porcine EIA and ICA as well as human dermal fibroblasts. There was a six log reduction in copy number in acellular CFA when compared to fresh and a seven log reduction for acellular ICA. The copy number present within acellular ICA and EIA was significantly lower than any of the commercially available products, as there are no established minimum safe levels of porcine endogenous retroviruses compared to commercially available products is critical. The assay does not determine whether the entire PERV genome is present or if it is transcriptionally active. The biomechanical properties and compliance of acellular porcine EIA and ICA were evaluated through burst pressure testing, suture retention testing, dilation testing and low strain rate failure testing. It is essential that any graft material has similar biomechanical characteristics to the arteries they are replacing. There were no major changes in the properties of acellular porcine vessels compared to fresh porcine tissue. There were no significant differences noted between the burst pressures of acellular EIA or ICA compared to fresh vessels. The burst pressure values were much higher than normal physiological pressures experienced within arteries which are in the region of 120 mmHg. The results obtained for the acellular arteries were comparable to the maximum burst pressures of human arteries (2031-4225 mmHg) and human saphenous vein (1680-2273 mmHg; L'Heureux, N. et al., 2006).

As regards complement activation and detection of C3a or C5a (FIG. 20) the acellular vessels produced by the methods of the present invention show negligible activation as compared to commercially available products and also interestingly as compared to porcine ureter prepared by the same methods. This indicates that there has been a successful ablation of antigenic epitopes from the two acellular vessel tissues.

The data collected to date demonstrates two sterile acellular vessels can be reliably produced using a novel decellularisation protocol which results in a biocompatible vessel demonstrating a >90% (w/w) reduction in DNA, minimal α-Gal levels and is not biochemically or biomechanically distinct from fresh vessels. Additionally, data showed the PERV content of acellular EIA and ICA to be significantly lower than commercially available products which have a proven clinical record of use in patients.

Decellularisation of Porcine External Iliac Arteries (EIA) and Internal Carotid Arteries (ICA)

Frozen EIA and ICA vessels of up to 200 mm in length were prepared as described in FIG. 1 using 200 ml of each solution wherein each solution is pre warmed to the appropriate temperature before use. Vessels are placed into individual 250 ml sterile containers and all incubations are carried out with agitation at 240 rpm with the exception of the nuclease step which is at 80 rpm. As a first step, if the EIA and ICA is frozen the tissue is thawed at 37° C. for 20 minutes, then washed using disinfection solution comprising vancomycin, gentamicin sulphate and polymyxin B for 30 minutes at 37° C. The first incubation step is a wash using 200 mM EDTA at 4° C. for 24 hours, followed by a wash using hypotonic buffer (10 mM TRIS, 2.7 Mm EDTA, 10 KIU/ml aprotinin) 4° C. for 24 hours and a wash using 0.1% (w/v) SDS in hypotonic buffer at 37° C. for 24 hours. A further wash using hypotonic buffer at 4° C. for 24 hours is followed by a wash using DPBSa EDTA containing aprotinin for between 48-56 hours at 4° C. and a wash using 0.1% (w/v) SDS in hypotonic buffer at 37° C. for 24 hours. The tissue is then washed three times using DPBSa at 37° C. for 30 minutes each and a nuclease solution (5 mM TRIS, 50 µg/ml BSA, 50 U/ml DNAase, 1 U/ml RNAase) at 37° C. for three hours. The tissue is then washed three times using DPBSa EDTA containing aprotinin at 37° C. for 30 minutes each and a further incubation wash using hypertonic solution for 24 hours at 37° C. and three further washes using DPBSa EDTA containing aprotinin at 37° C. for 30 minutes each. The tissue is then sterilised using 0.1% (v/v) peracetic acid solution for four hours at 27° C. The following subsequent steps are carried out aseptically inside a class II safety cabinet, (i) wash three times using DPBSa EDTA containing aprotinin at 37° C. for 30 minutes each (ii) wash using DPBSa at 4° C. for 24 hours. Tissue is then stored in DPBSa at 4° C. until needed.

Tissue/Histology Preparation

Tissue specimens were fixed in 10% (v/v) neutral buffered formalin and then dehydrated and embedded in paraffin wax. Serial sections were taken and standard haematoxylin and eosin (H&E) (Bios Europe Ltd, Skelmersdale, UK) staining was used to evaluate tissue histioarchitecture and Miller's elastin staining was used to evaluate the elastin content. Nucleic acids were stained using DAPI stain (Sigma-Aldrich) and Hoechst 33258 (Sigma-Aldrich). Monoclonal antibodies IgM against α-Gal epitope were obtained from Alexis biochemicals, San Diego, USA and purified before use.

Antibody Adsorption Assay for α-Gal

ELISA was used to determine the levels of unbound α-Gal antibody following incubation with tissue samples. Samples were incubated with 500 µl 5% (w/v) BSA in DPBS overnight at 4° C., the BSA was then disposed and each tube was washed three times for two minutes using 500 µl DPBS. Exactly 100 mg of tissue was weighed and finely macerated and placed in blocked micro tubes with 1 ml anti α-gal monoclonal antibody in antibody diluent (0.37 mg·ml$^{-1}$) and left overnight at 4° C. on a spinner. The tissue-containing micro tubes were centrifuged at 600×g for 15 minutes (or 13,000 rpm on micro-centrifuge) and 750 µl supernatant was removed to fresh blocked micro tubes to which a further 750 µl TBS azide BSA was added and then mixed and centrifuged at 600×g for 15 minutes. A further 750 µl supernatant was removed and the supernatant assayed for antibody to α-Gal by ELISA by adding 50 µl of α-Gal BSA at 10 µg·ml$^{-1}$ in DPBS to Maxisorb microtitire plate wells overnight at 4° C. These were washed 3×10 min using 300 µl DPBS Tween with agitation, and each well of the coated Maxisorb microtitire plate was blocked with 250 µl 5% (w/v) BSA in DPBS overnight at 4° C. Subsequently each well was washed ×3 for 30 min using 300 µl DPBS Tween with agitation and 100 µl of samples was transferred to relevant wells of coated and blocked microtitire plate. This was then incubated at room temperature for three hours and further washed before addition of 50 µl horseradish peroxidase-conjugated secondary rabbit anti-mouse antibody (1:1000 dilution). This was incubated for 1 hr at room temperature and further washed before adding 100 µl OPD solution and incubating for 10 min at room temperature, in the dark. 50 µl 3M sulphuric acid was added to each well and the optical densities were measured using a micro plate spectrophotometer at 492 nm with a reference filter at 630 nm. The values of each sample were plotted as a mean±95% confidence limits and any significant difference determined.

Hydroxyproline Assay.

Prior to performing the hydroxyproline assay, samples were lyophilized to a constant weight before being hydrolysed by incubation with 6M hydrochloric acid (HCL) for 4 h at 120° C. and neutralized using sodium hydroxide (NaOH). The procedure adopted was based on the method described by Edwards and O'Brien [29]. Standard calibrator solutions were made up using trans-4-hydroxy-L-proline (Sigma). Test solution (50 µl) was added to wells of a flat bottomed 96-well plate to which 100 µl of oxidizing solution (chloramine T hydrate; Sigma) was added and left for 5 min with gentle agitation. Ehrlich's reagent (100 µl) was then added to each well. The plate was then covered and incubated at 60° C. in a water bath for 45 min prior to the absorbance being read at 570 nm. The concentration of hydroxyproline was then determined by interpolation from a hydroxyproline standard curve.

Glycosaminoglycan Assay

The amount of sulphated sugars (GAGs) was determined by dimethylmethylene blue binding (Enobakhare et al, Anal. Biochem. 243, 189, 1996; Farndale et al, Biochim. Biophys. Acta., 883, 173, 1986). Briefly, test solutions were incubated with the dimethylmethylene blue solution and the absorbance read at 525 nm. The amount of GAGs was calculated by interpolation from a standard curve prepared using chondroitin sulphate and phosphate assay buffer (0.1M sodium di-hydrogen orthophosphate, 0.1M di-sodium hydrogen orthophosphate, pH6.8) over a range of concentrations.

EXAMPLE 1

Figure 3:
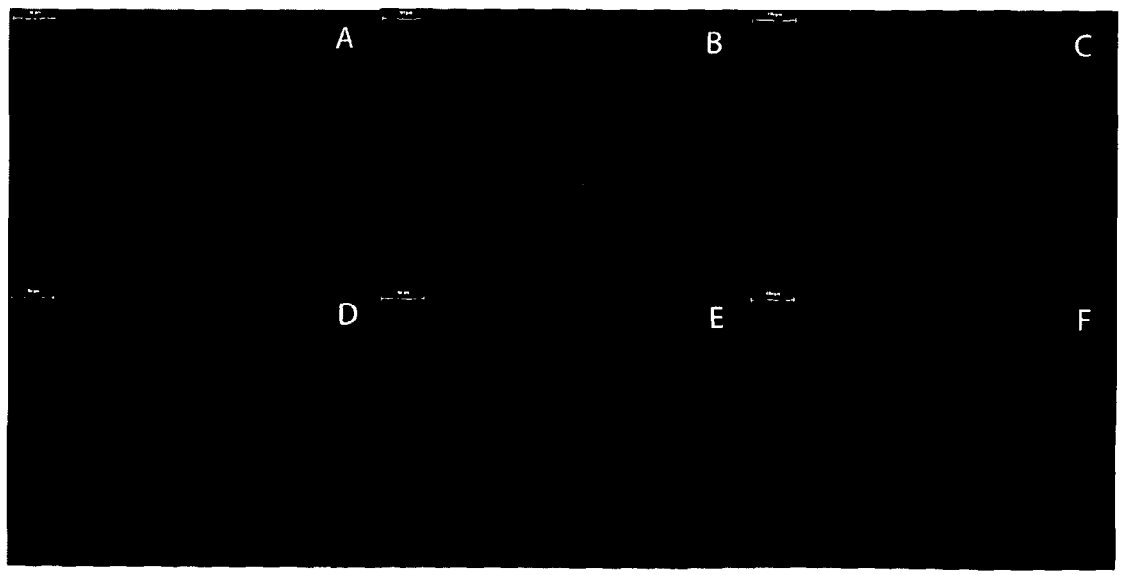
FIG. 3 shows porcine ICA (C-D) and EIA (E-F) treated using two cycles of hypotonic buffer and SDS solution (1 mg·ml$^{-1}$) and stained using DAPI. Fresh porcine ICA (A) and EIA (B) were used as positive controls.
Figure 2:
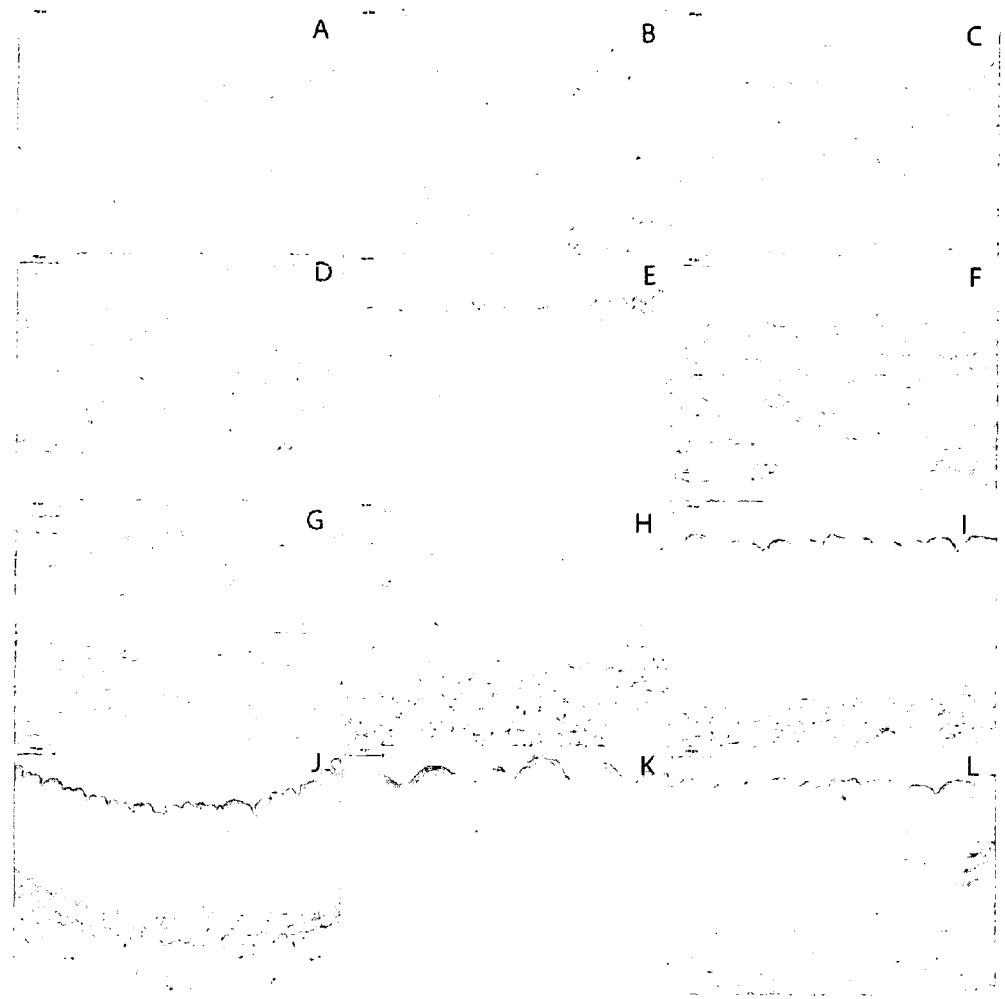
FIG. 2 shows porcine internal carotid (ICA) in FIGS. 2 A-H and external iliac arteries (EIA) in Figures I-L treated using two cycles of hypotonic buffer and SDS solution (1 mg·ml$^{-1}$) and then stained using haematoxylin and eosin.

Formalin fixed treated porcine ICA and EIA was sectioned at 5 µm and stained using haematoxylin and eosin (FIG. 2). When two cycles of hypotonic buffer and SDS were used there was no evidence of residual cells or cellular remnants (FIG. 2). Additionally the matrix histoarchitecture appeared to have remained intact following treatment. Sections of formalin fixed treated porcine ICA and EIA were stained for the presence of double stranded DNA using DAPI, fresh porcine ICA and EIA were used as positive controls (FIG. 3). The staining demonstrated a lack of double stranded DNA and cells within the matrix compared to fresh control tissue (FIG. 3). When the exposure time was increased by a factor of ten no fluorescence was apparent as a result of the presence of double stranded DNA and therefore cells.

EXAMPLE 2

Figure 4:
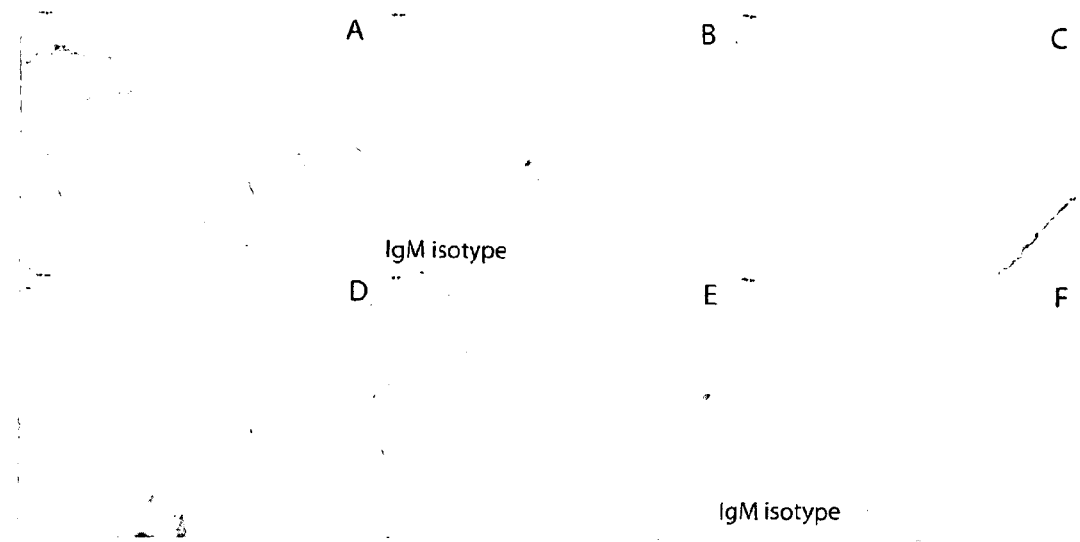
FIG. 4 shows fresh (C) and acellular porcine EIA treated using two cycles of hypotonic buffer and SDS solution (1 mg·ml$^{-1}$), Figures D and E are labelled using a monoclonal antibody against the α-Gal epitope, or an isotype control (F). Fresh porcine skin was used as a positive control (A, B).
Figure 5:
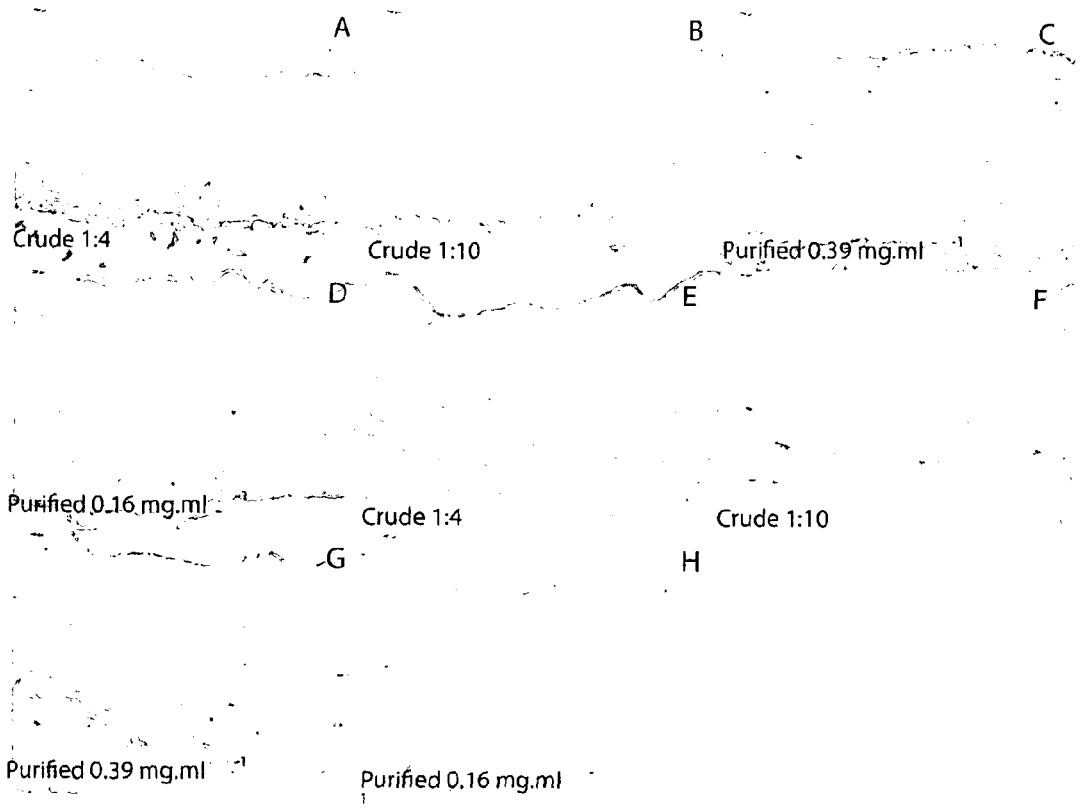
FIG. 5 shows acellular ICA treated using 200 mM EDTA at 4° C. (E-) and one cycle of hypertonic buffer at 37° C. and labelled using a monoclonal antibody against the α-Gal epitope.

It is desirable that acellular xenogeneic matrices are devoid of the α-Gal epitope if they are to be used clinically in order to mitigate against antibody mediated inflammatory reactions. Therefore it is necessary to develop a reliable method to detect its presence within the acellular vessels. Samples of fresh and acellular porcine EIA (two cycles SDS) were formalin fixed, embedded into paraffin wax and sectioned at 5 µm. Sections of fresh and acellular porcine EIA were labelled for the presence of the α-Gal epitope using an IgM monoclonal antibody (Alexis 801-090, clone M86, dilution 1:10). The Dako Envision kit was used to visualise the primary antibody (FIG. 4). The results demonstrated the presence of the α-Gal epitope following decellularisation. There was also a high degree of background staining; this was absent when an IgM isotype control antibody was used to label the samples. Further experiments showed that the fresh tissue demonstrated good positive labelling with the IgM monoclonal antibody (data not shown) and that the purified antibody appeared to produce a greater specificity of labelling compared to the crude preparation (data not shown). The labelling demonstrated a reduction in α-Gal content when hypertonic buffer was used in conjunction with a 200 mM EDTA wash carried out at 4° C. for 24 hours (FIG. 5). There was no difference in the levels of α-Gal content when increasing cycles of hypertonic buffer were used. Therefore one 24 hour incubation in hypertonic buffer at 37° C. was adopted to remove the α-Gal epitope from acellular matrices in conjunction with an initial 200 mM EDTA wash carried out at 4° C. for 24 hours. For subsequent tissue decellularisation protocol in FIG. 1 was adopted.

EXAMPLE 3

Figure 6:
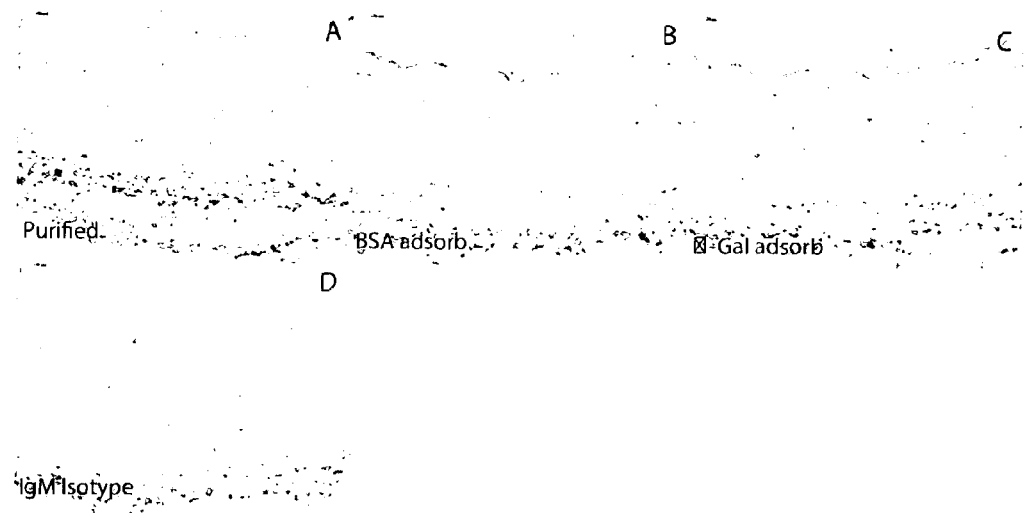
FIG. 6 shows acellular EIA prepared according to the protocol of FIG. 1 and labeled using a monoclonal antibody against the α-Gal epitope, purified (A), adsorbed against BSA (B) or adsorbed against α-Gal BSA (C) or an IgM isotype control (D).
Figure 7:
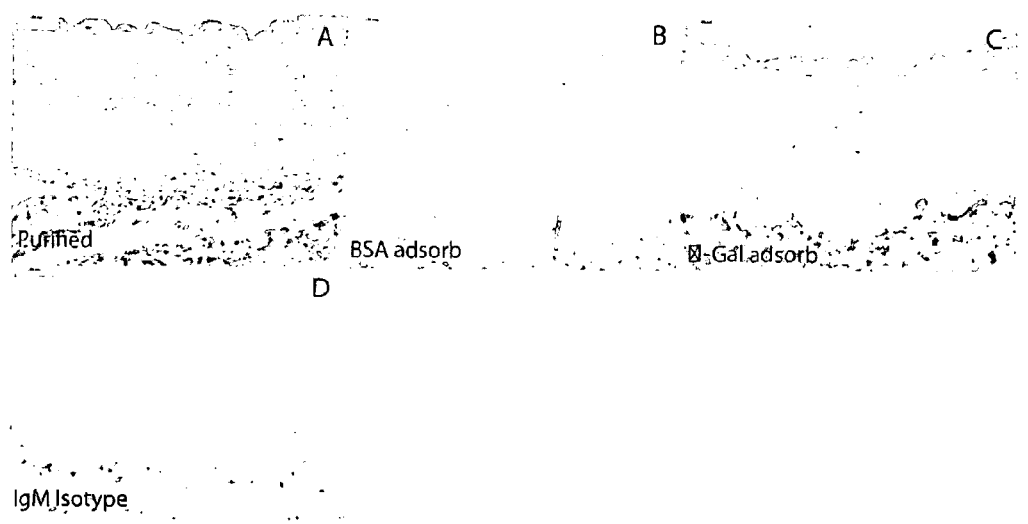
FIG. 7 shows acellular ICA labeled using a monoclonal antibody against the α-Gal epitope, purified (A), adsorbed against BSA (B) or adsorbed against α-Gal BSA (C) or an IgM isotype control (D).

In order to determine if there was residual α-Gal present within the acellular vessels it was important to determine the specificity of the antibody labelling. Samples of fresh and acellular EIA and ICA along with fresh and acellular α-galactosidase treated EIA and ICA were labelled for the presences of the α-Gal epitope using an IgM monoclonal antibody (Alexis ALX-801-090) clone M86 and visualised using the Dako Envision kit. Three different preparations of the antibody were used: (i) purified antibody (1:4 dilution-0.39 mg·ml$^{-1}$) (ii) purified antibody adsorbed using BSA and (iii) purified antibody adsorbed using α-Gal BSA. FIG. 6 shows acellular EIA labeled using a monoclonal antibody against the α-Gal epitope, purified (A), adsorbed against BSA (B) or adsorbed against α-Gal BSA (C) or an IgM isotype control (D) with original magnification×100. FIG. 7 shows the same but for acellular ICA.

Antibody labelling of fresh tissue demonstrated strong defined positive labelling throughout the matrix; this could be significantly reduced upon α-galactosidase treatment. The results indicated the purified antibody was further "cleaned" by absorption with BSA. The "purified" antibody absorbed with BSA is specific for α-Gal since absorption with α-Gal BSA totally ablated binding to fresh tissue. Furthermore, there was minimal α-Gal present within acellular ICA and EIA, the luminal surface was totally clear. Close inspection of sections by microscopy revealed that any background labelling with the BSA absorbed antibody was minimal. The study further demonstrated the background labelling cannot be removed by treatment using α-galactosidase.

EXAMPLE 4

Figure 8:
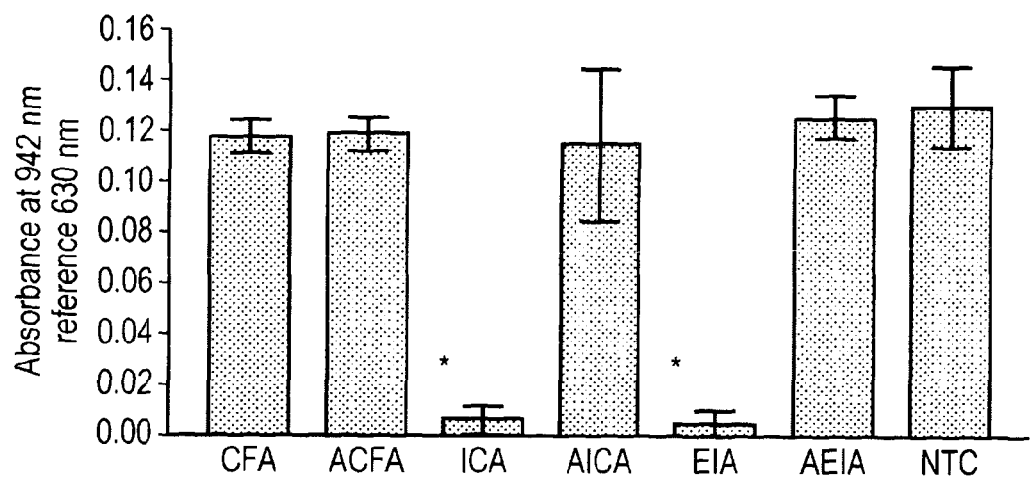
FIG. 8 shows ELISA for detection of antibodies to the α-Gal epitope following adsorption with fresh and acellular, porcine and human allogeneic vessels. Data is expressed as mean (n=6)±95% confidence limits. * represents a significant difference as determined by one-way ANOVA and post hoc T test. ICA fresh porcine ICA; AICA acellular porcine ICA; CFA fresh human common femoral artery; ACFA acellular human common femoral artery; EIA fresh porcine external iliac artery; AEIA acellular porcine external iliac artery; NTC no tissue controls.

A semi quantitative antibody adsorption assay was used to estimate the amount of α-Gal present in porcine tissues. An ELISA was used to quantify unbound anti α-Gal antibody present following incubation with macerated tissue samples. The negative control used was a no tissue control and the data indicated there to be a significant difference between the no tissue control, acellular vessels, and human skin. Fresh and acellular allogeneic common femoral arteries were used as controls for this assay (FIG. 8). The assay showed fresh and acellular common femoral arteries to be free from the α-Gal epitope. There was no significant difference in the α-Gal antibody binding to acellular porcine EIA or ICA compared to the no tissue control, or fresh and acellular allogeneic common femoral arteries (FIG. 8). However, there was a significant difference between the antibody bound to acellular compared to fresh EIA and ICA (FIG. 8; one way ANOVA and post hoc T test).

EXAMPLE 5

In order to fully evaluate the effects of the decellularisation protocol on the matrtices Samples of fresh and acellular EIA and ICA (n=6) were assayed to determine their major components. To quantify collagen acid hydrolysed tissue samples were assayed for hydroxyproline content following the method of Edwars & O'Biran (1980). The assay generated a linear relationship between a standard curve produced using Trans-4-HYDROXY-L-PROLINE and absorbance at 570 nm. The assay values were converted to µg·mg$^{-1}$ and hydroxyproline values were converted to collagen by multiplication by 7.46. The collagen content of fresh and acellular ICA was found to be 795.2 µg·mg$^{-1}$ and 700.6 µg·mg$^{-1}$ respectively. The collagen content of fresh and acellular EIA was 572.3 µg·mg$^{-1}$ and 547.3 µg·mg$^{-1}$ respectively. The values were not significantly different (one-way ANOVA and post hoc T test).

Figure 9A:
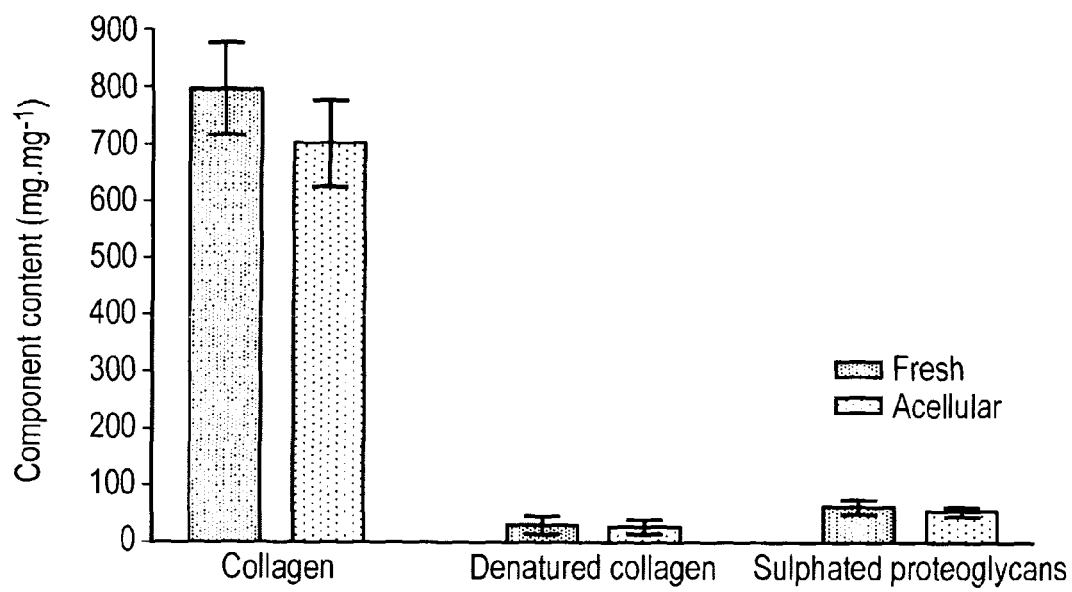
FIG. 9 shows collagen, denatured collagen and sulphated proteoglycan content of fresh and acellular porcine EIA (FIG. 9A) and ICA (FIG. 9B). Data is expressed as mean (n=6)±95% confidence limits.
Figure 9B:
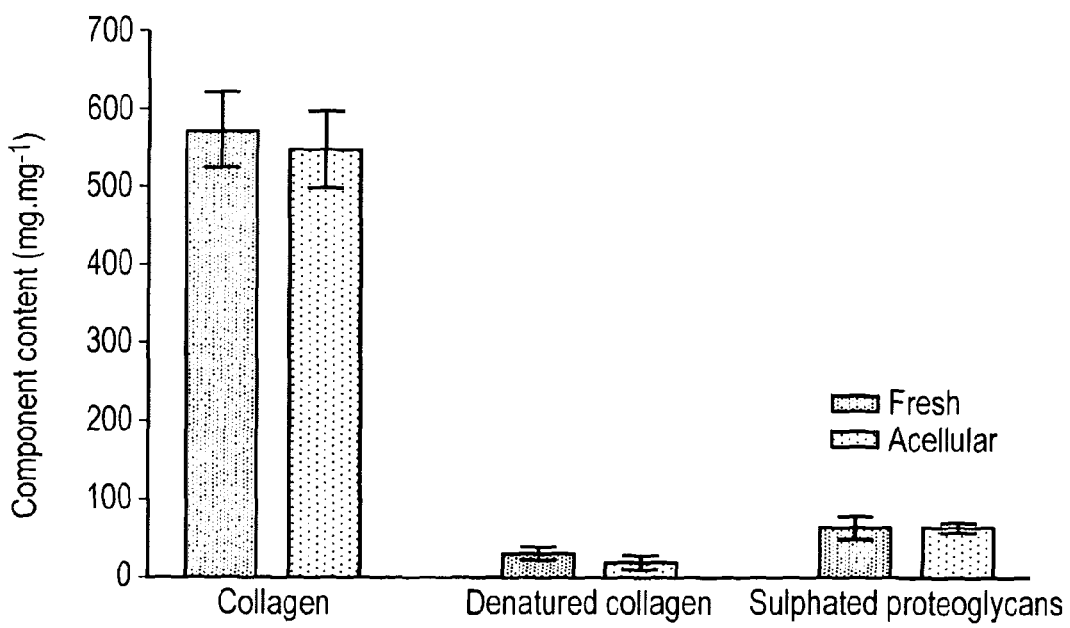

To quantify GAG content acid hydrolysed tissue samples were assayed for sulphated carboxylated sugar content using dimethylene blue dye (Farndale et al., 1986). The assay generated a linear relationship between a standard curve produced using Chondroitin sulphate B and absorbance at 525 nm the assay values were normlised for sample mass and expressed as µg·mg$^{-1}$. The sulphated GAG content of fresh ICA was determined to be 63.8 µg·mg$^{-1}$ compared to acellular ICA which was 57.0 µg·mg$^{-1}$. The GAG content of fresh and acellular EIA were found to be 64.5 µg·mg$^{-1}$ and 54.7 µg·mg$^{-1}$ respectively. The values were not significantly different (one-way ANOVA and post hoc T test; FIGS. 9A and 9B).

Denatured or damaged collagen content was assessed using enzymatic digestion of tissues using α-chymotrypsin followed by acid hydrolysis. Hydroxyproline levels were determined and converted to collagen. The assay generated a linear relationship between a standard curve produced using Trans-4-HYDROXY-L-PROLINE and absorbance at 570 nm. The denatured collagen content of fresh and acellular ICA was found to be 30.8 µg·mg$^{-1}$ and 26.6 µg·mg$^{-1}$ respectively. The denatured collagen content of fresh and acellular EIA was 30.8 and 21.5 µg·mg$^{-1}$ respectively. The values were not significantly different (one-way ANOVA and post hoc T test; FIGS. 9A and 9B).

EXAMPLE 6

Figure 10:
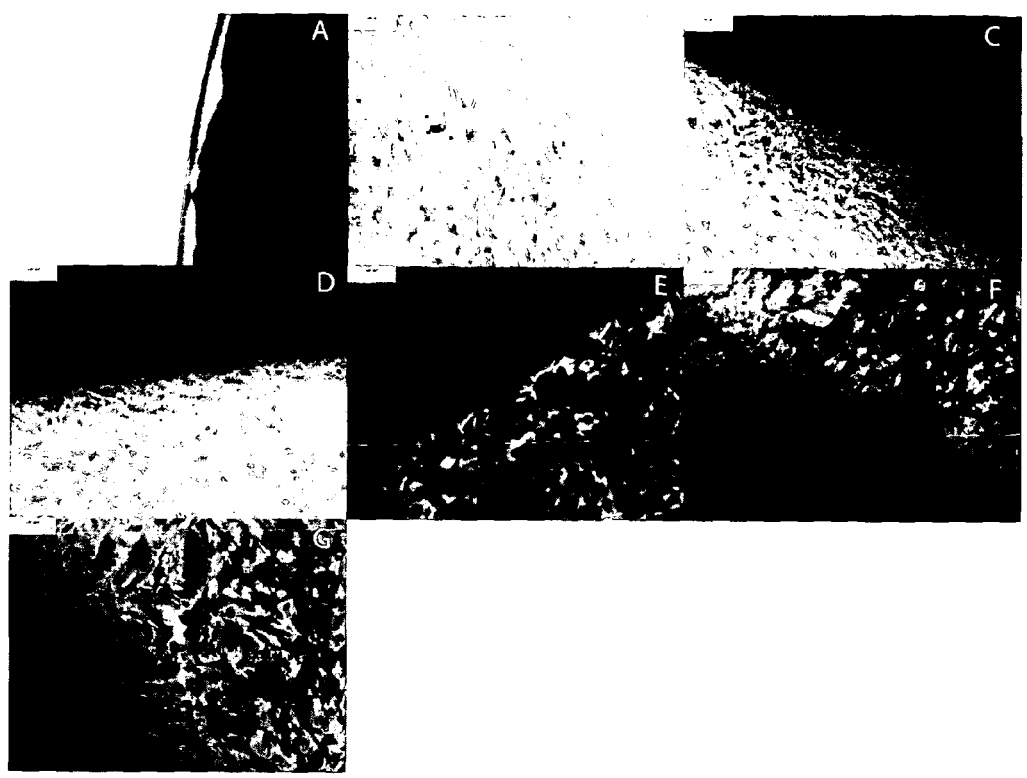
FIG. 10 shows baby hamster kidney cells cultured with cyanoacrylate contact adhesive (A) collagen gel (B, E), or acellular porcine EIA (C, F) and ICA (D, G) for 48 hours, viewed using phase contrast microscopy and stained using Giemsa's stain.
Figure 11:
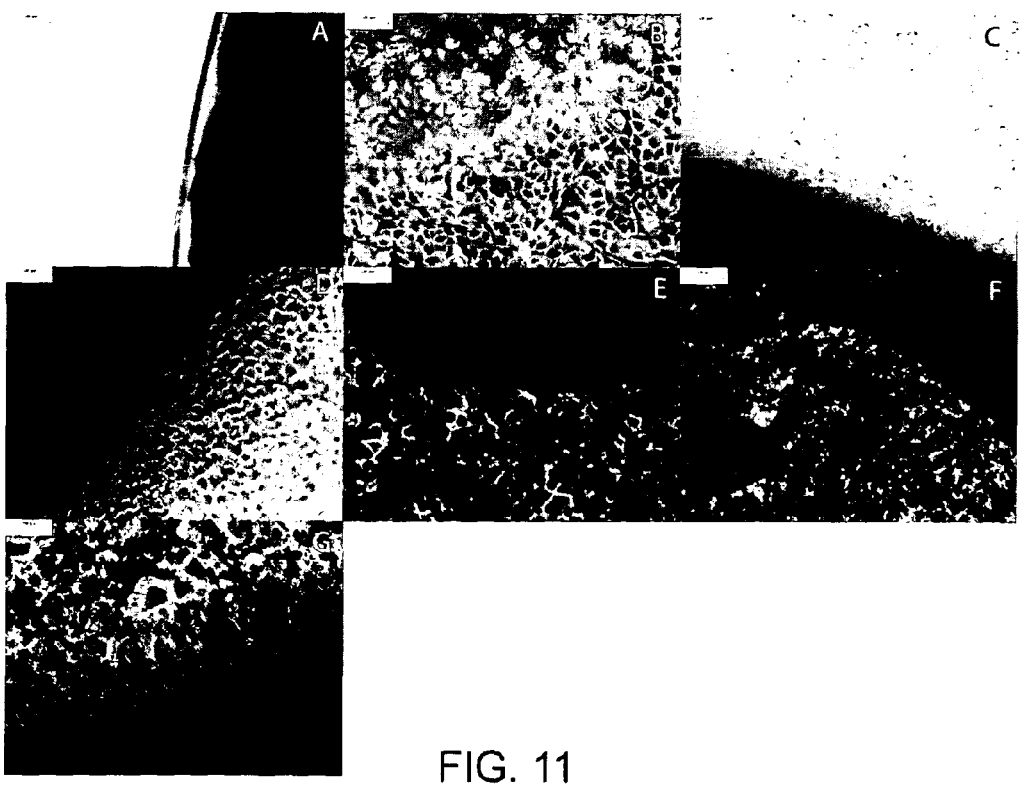
FIG. 11 shows murine 3T3 cells cultured with cyanoacrylate contact adhesive (A) collagen gel (B, E), or acellular porcine EIA (C, F) and ICA (D, G) for 48 hours, viewed using phase contrast microscopy and stained using Giemsa's stain.

The contact cytotoxicity assay was used to determine the effect of the acellular matrices on cell growth; this was used as a preliminary assessment of biocompatibility. Small samples acellular porcine EIA and ICA (n=3) were dissected aseptically and adhered to the centre of tissue culture plate wells using collagen gel, a suspension of either mycoplasma free mouse 3T3 or baby hamster kidney cells was added to each well and cultured for 48 hours. Each well was viewed using phase contrast microscopy and following formalin fixation and staining using Giemsa's stain. Microscopic examination of the contact cytotoxicity plates showed that the mouse 3T3 fibroblasts (FIG. 11) and baby hamster kidney cells (FIG. 10) grew up to and in contact with acellular material. No obvious changes in cell morphology or and cell lysis was noted. Cyanoacrylate glue (positive control) was shown to cause cell lysis. Collagen alone (negative control) showed no signs of cytotoxicity.

EXAMPLE 7

Figure 12A:
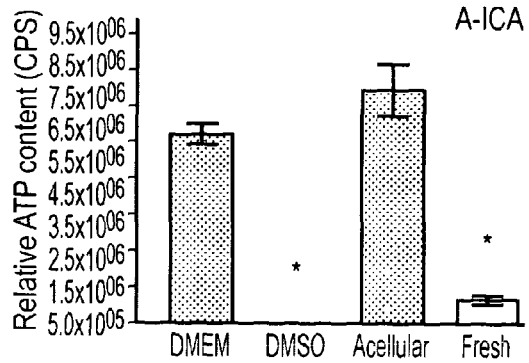
FIG. 12 shows relative ATP content of mouse 3T3 cells incubated with fresh or acellular porcine EIA (FIG. 12B) and ICA (FIG. 12A) extract samples or baby hamster kidney cells incubated with fresh or acellular porcine EIA (FIG. 12D) and ICA (FIG. 12C) extract samples each sample being incubated with DMSO 40% (v/v) was used as a positive control for cytotoxicity and DMEM as a negative control for cytotoxicity. Data is expressed as mean (n=6)±95% confidence limits. * Represents a significant difference to the DMEM control as determined by one-way ANOVA and post hoc T test.
Figure 12B:
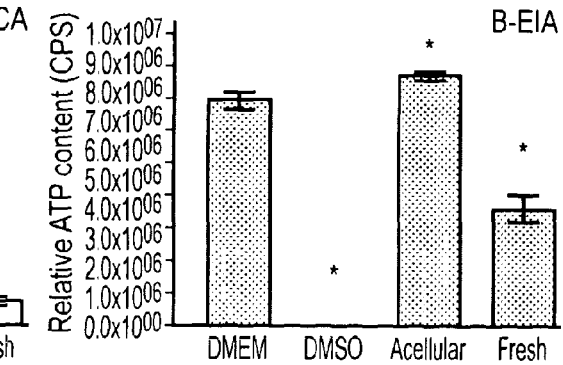
Figure 12C:
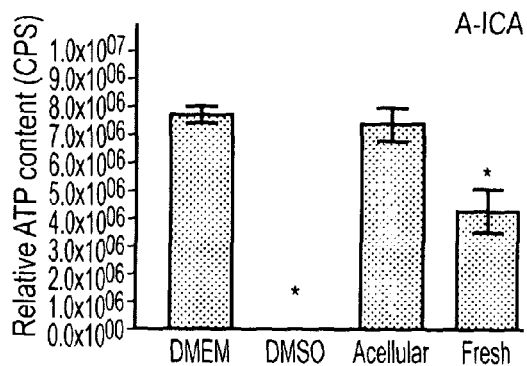
Figure 12D:
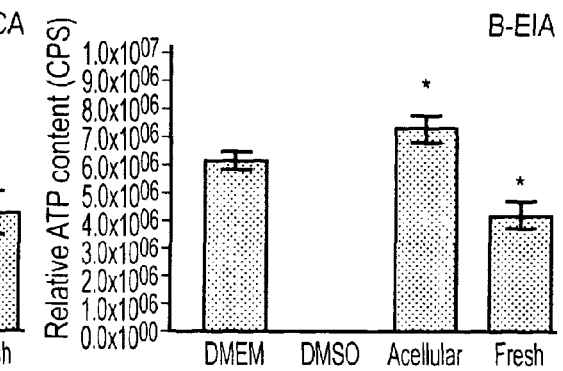

Samples of fresh and decellularised porcine EIA and ICA were macerated and incubated at a concentration of 100 mg·ml$^{-1}$ in DMEM at 37° C. with agitation for 72 hours in order to extract any soluble components. This extract was incubated along with a monolayers of mycoplasma free mouse 3T3 and baby hamster kidney cells for 48 hours, following which the levels of ATP were determined using the commercially available ATP-Lite-M assay (Perkin Elmer). Two different cell lines were used; mouse 3T3 cells a fibroblastic cell line and baby hamster kidney cells an epithelial cell line. The results demonstrated no significant difference between the relative ATP content and therefore viability of mouse 3T3 cells incubated with DMEM and extracted samples of acellular porcine ICA (FIGS. 12A and 12B). There was a significant increase in cell viability when mouse 3T3 cells were incubated with extracts of acellular porcine EIA (FIG. 12B). There was a significant difference between the ATP content of 3T3 cells incubated with DMEM or acellular extracts compared to fresh tissue extracts (FIG. 12A). The levels of ATP present within 3T3 cells cultured in the presence of 40% (v/v) DMSO were significantly lower than any of the other samples tested (FIGS. 12A and 12B). There was a significant increase in ATP levels of baby hamster kidney cells cultured with extracts of acellular porcine EIA or ICA compared to DMEM (FIGS. 12C and 12D). There was no significant difference between the ATP content of baby hamster kidney cells incubated with DMEM or acellular extracts compared to fresh tissue extracts (FIGS. 12C and 12D). The levels of ATP present within baby hamster kidney cells cultured in the presence of 40% (v/v) DMSO were significantly lower than any of the other samples tested (FIGS. 12C and 12D).

EXAMPLE 8

Figure 13:
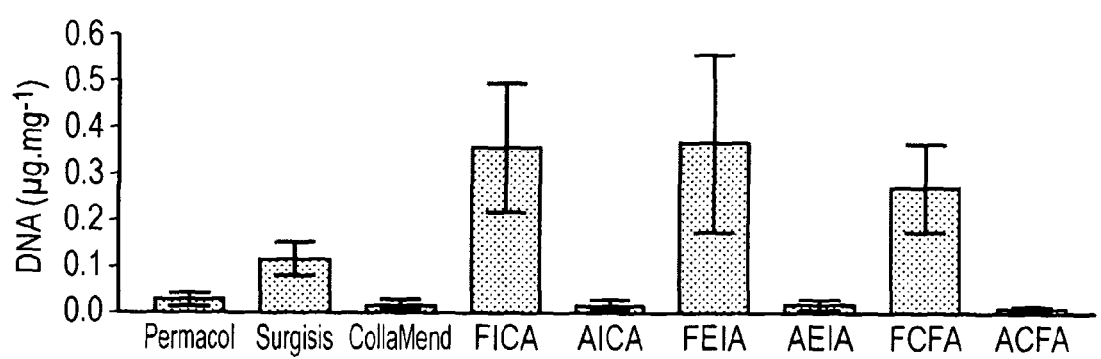
FIG. 13 shows quantification of DNA extracted from fresh and acellular porcine EIA and ICA, fresh and acellular human common femoral arteries (CFA), Surgisis, Permacol, and CollaMend using absorbance at 260 nm. Data is expressed as mean (n=3)±95% confidence limits

DNA was isolated from samples (n=3) of fresh and acellular porcine EIA and ICA using a commercially available kit (Qiagen) and quantified using absorbance at 260 nm. A number of commercially available products were also included in the analysis: Surgisis, Permacol, and CollaMend. The data indicated there to be a greater than 90% reduction in DNA levels following decellularisation. Acellular EIA and ICA contained 0.014 µg·mg$^{-1}$ and 0.019 µg·mg$^{-1}$ respectively of DNA (FIG. 13). Surgisis contained 0.119 µg·mg$^{-1}$, [1] Permacol 0.028 µg·mg$^{-1}$ and CollaMend 0.017 µg·mg$^{-1}$ of DNA (FIG. 13). Acellular EIA and ICA contained a significantly lower amount of DNA than Surgisis (FIG. 13).

EXAMPLE 9

PCR and RT-PCR was carried out using extracted DNA and total RNA. Primers against GAPDH and TNFα were used to amplify DNA extracted from fresh and acellular EIA and ICA. The fluorescent dye syber green was used to detect any PCR products. The PCR reaction failed to detect any GAPDH or TNFα products in samples of DNA extracted from acellular EIA or ICA (Table 1). Therefore any DNA present was likely to be fragments and non-coding and thus non-functional DNA merely for "house-keeping" activities.

Table 1 shows the cycle number at which PCR products were detected when primers against GAPDH and TNFα were used against isolated DNA in a syber green PCR.

| Sample | Primer | Threshold value | Ct value |
| --- | --- | --- | --- |
| Fresh EIA | GAPDH | 0.210 | 33.75 |
| Acellular EIA | GAPDH | 0.210 | No ct value |
| Acellular ICA | GAPDH | 0.210 | No ct value |
| Fresh EIA | NPC | 0.210 | No ct value |
| Acellular EIA | NPC | 0.210 | No ct value |
| Acellular ICA | NPC | 0.210 | No ct value |
| Fresh EIA | TNFα | 0.210 | 29.99 |
| Acellular EIA | TNFα | 0.210 | No ct value |
| Acellular ICA | TNFα | 0.210 | No ct value |
| No template control | GAPDH | 0.210 | No ct value |
| No template control | TNFα | 0.210 | No ct value |

Detection of GAPDH (Table 2) and TNFα (Table 3) was carried out using a two step RT-PCR reaction of total RNA extracted from fresh and acellular EIA and ICA. The fluorescent dye syber green was used to detect any PCR products. The RT-PCR reaction failed to detect any GAPDH or TNFα products in samples of total RNA extracted from acellular EIA or ICA when compared to fresh samples.

Table 2 shows the cycle number at which PCR products were detected when primers against GAPDH are used against isolated RNA in a two step RT-PCR.

| Sample | Primer | Threshold value | Ct value |
| --- | --- | --- | --- |
| Fresh EIA | GAPDH | 0.212 | 47.03 |
| Acellular EIA | GAPDH | 0.212 | No ct value |

-continued

| Sample | Primer | Threshold value | Ct value |
|---|---|---|---|
| Fresh ICA | GAPDH | 0.212 | 49.14 |
| Acellular ICA | GAPDH | 0.212 | No ct value |
| No template control | GAPDH | 0.212 | No ct value |
| Fresh EIA | No primer control | 0.212 | No ct value |
| Acellular EIA | No primer control | 0.212 | No ct value |
| Fresh ICA | No primer control | 0.212 | No ct value |
| Acellular ICA | No primer control | 0.212 | No ct value |

Table 3 shows the cycle number at which PCR products were detected when primers against TNFα are used against isolated RNA in a two step RT-PCR.

| Sample | Primer | Threshold value | Ct value |
|---|---|---|---|
| Fresh EIA | TNFα | 0.123 | 37.52 |
| Acellular EIA | TNFα | 0.123 | No ct value |
| Fresh ICA | TNFα | 0.123 | 36.78 |
| Acellular ICA | TNFα | 0.123 | No ct value |
| No template control | TNFα | 0.123 | No ct value |
| Fresh EIA | No primer control | 0.123 | No ct value |
| Acellular EIA | No primer control | 0.123 | No ct value |
| Fresh ICA | No primer control | 0.123 | No ct value |
| Acellular ICA | No primer control | 0.123 | No ct value |

EXAMPLE 10

Detection and quantification of porcine endogenous retroviruses was carried out using Quantitative real time PCR utilising a taqman probe. DNA was isolated from samples (n=3) of fresh and acellular porcine EIA and ICA using a commercially available kit (Qiagen) and quantified using absorbance at 260 nm. A number of commercially available products were also included in the analysis: Surgisis, Permacol, and CollaMend. DNA was also isolated from primary human dermal fibroblasts obtained from a commercial source.

Table 4 shows the copy number of PERV genome present within porcine, EIA, ICA, Permacol, CollaMend, Surgisis, and primary human fibroblasts. The data represents mean (n=3).

| Sample | Ct value | Copy No. |
|---|---|---|
| Fresh EIA | 22.54 | 4.52E+05 |
| Acellular EIA | 36.76 | 2.54E−01 |
| Fresh ICA | 23.94 | 2.61E+05 |
| Acellular ICA | 38.21 | 8.32E−02 |
| Permacol | 32.14 | 5.92 |
| CollaMend | 35.21 | 13.46 |
| Surgisis | 31.02 | 2.54E+01 |
| Fibroblasts | 18.44 | 2.30E+01 |
| NTC | No ct value | N/A |

The data indicated PERV DNA to be present in all samples tested (Table 4). There was a six log reduction in copy number in acellular CFA when compared to fresh and a seven log reduction for acellular ICA. The copy number present within acellular ICA and EIA was significantly lower than any of the commercially available products (one way ANOVA and post hoc T test). The assay does not determine whether the entire PERV genome is present or if transcriptionally active.

EXAMPLE 11

Samples of fresh and acellular porcine EIA and ICA (15 cm in length) were tested for their ability to withstand increasing pressure using a custom designed burst pressure rig. The internal pressure was increased to a maximum of 3750 mmHg for each vessel. Acellular porcine EIA which had been treated using 0.1% (v/v) peracetic acid for three or four hours was tested to determine if this step had a detrimental effect on matrix biomechanics. The results demonstrated there to be no significant difference between the maximum pressures able to be withstood by fresh or acellular porcine EIA or ICA (data not shown). Two of the fresh samples failed at the region of ligation using sutures and none of the acellular samples failed as a result of set up or at the ligation or attachment sites. The mean burst pressure of acellular ICA was 3624 mmHG compared to 3750 mmHG for acellular EIA. There was no significant difference between acellular EIA which had been treated with 0.1% (v/v) peracetic acid for three or four hours.

EXAMPLE 12

Figure 14:
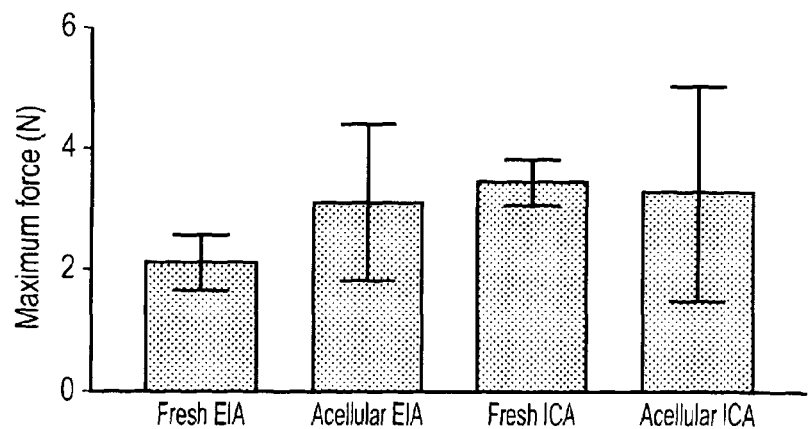
FIG. 14 shows suture retention testing of fresh and acellular porcine EIA and ICA. Data is expressed as mean (n=6)±95% confidence limits.

Suture retention testing was performed on acellular porcine EIA and ICA, the data was compared to fresh samples. A single suture was placed into the tissue sample using 4-0 Prolene and secured using a triple knot. The test was carried out using an Instron 5860 series table model testing systems at a speed of 10 mm·min$^{-1}$. The data was presented as the maximum force in Newton's each tissue was able to withstand before the suture was removed. There were no significant differences between maximum suture retention strength of fresh EIA or ICA compared to acellular samples (FIG. 14).

EXAMPLE 13

Figure 15:
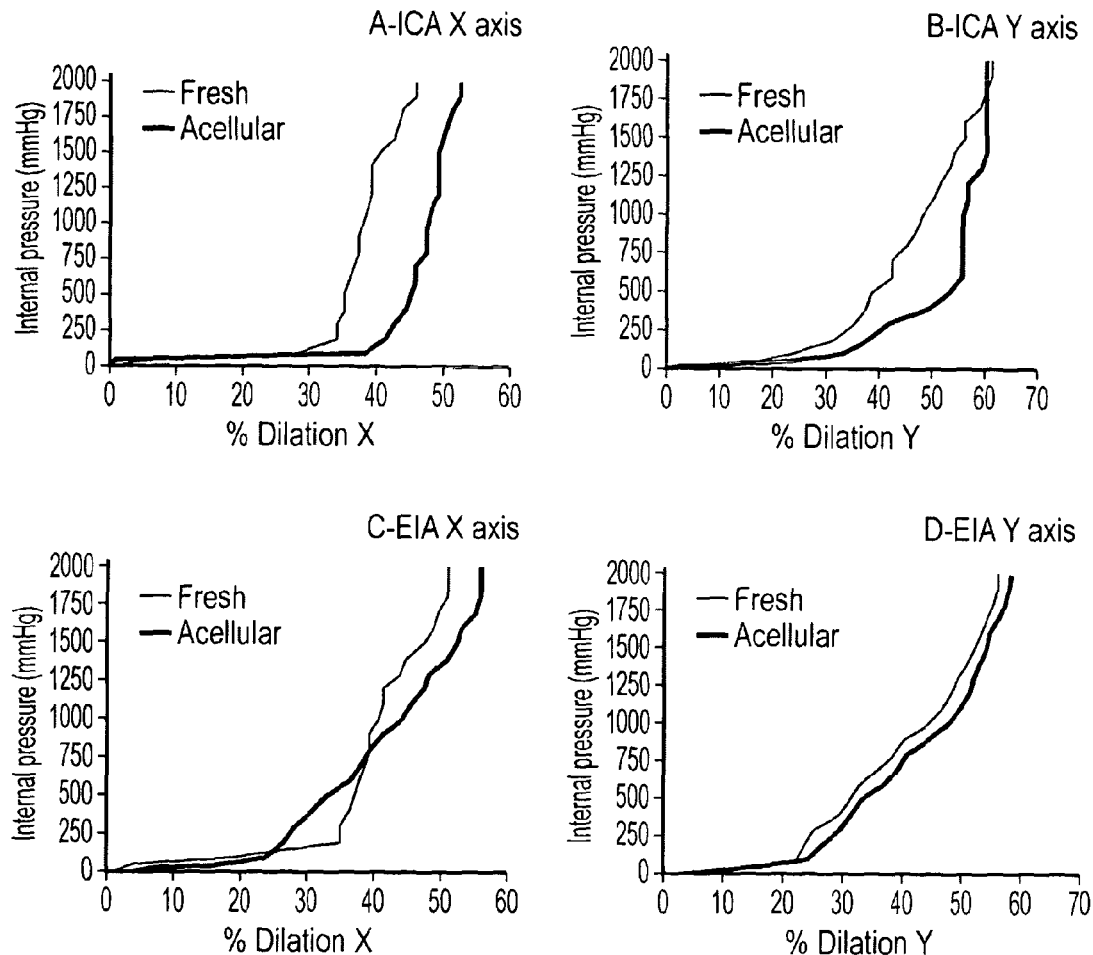
FIG. 15 shows dilation testing of fresh and acellular porcine ICA (A, B) and EIA (C, D) the data represents percentage change in root diameter as a function of increasing internal pressure. X axis (A, C) or Y axis (C, D). Data is expressed as mean (n=3)±95% confidence limits, the data has been arcsine transformed in order to perform statistical analysis on and back transformed.

The intention of this study was to quantify the circumferential and axial expansion of fresh and acellular porcine EIA and ICA (n=3). The data acquired during dilation testing included still images of fresh and acellular porcine EIA and ICA at the incrementally applied pressure intervals (n=3). All images were analysed in image pro plus V 5.41 software. The dilation in both the X and Y axis was determined. The results were presented as percentage change in root diameter as a function of increasing internal pressure (FIGS. 15A-D). The data demonstrated two statistically significant results; the dilation of acellular ICA in the X axis (FIG. 15A) was significantly greater than the dilation of fresh ICA. Additionally the dilation of acellular porcine ICA was greater than that of fresh ICA in the Y axis (FIG. 15B). Each of the other dilation curves was similar and demonstrated no significant differences between fresh and acellular tissues (FIG. 15A-D).

EXAMPLE 14

Figure 16:
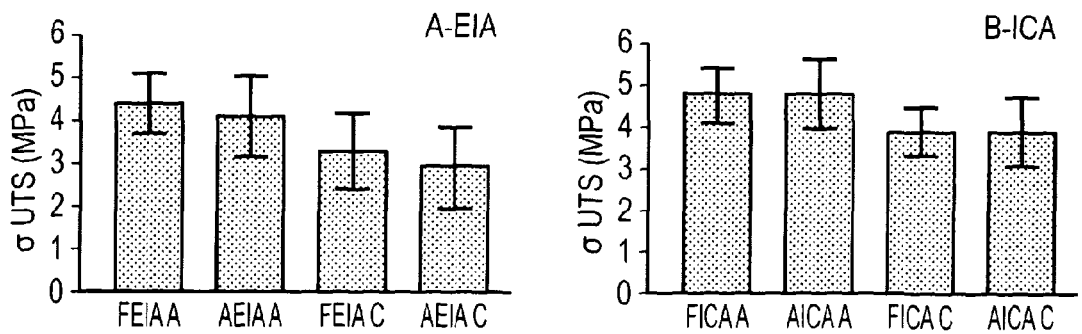
FIG. 16 shows circumferential and axial ultimate tensile strength of fresh and acellular porcine EIA (A) and ICA (B). Data is expressed as mean (n=6)±95% confidence limits.

Samples of fresh and acellular porcine EIA and ICA were testing using an Instron 5860 series table model testing systems at a speed of 10 mm·min$^{-1}$. During the low strain rate failure testing the stroke of the crosshead in mm, the response of the load transducer and the time in ms were recorded for the duration of each test. The dimensions of each tissue sample was standardised and the thickness recorded using a thickness gauge before mounting into the test rig. Each test was carried out in both axial and circumferential directions (n=6). The data was analysed using Microsoft excel and GraphPad Prism and stress strain curves produced for each sample. The following parameters were determined using the data and stress strain curves: ultimate tensile strength (N), Collagen and elastic modulus (MPa; FIGS. 16, 17 and 18).

The data demonstrated no significant differences in the mechanical properties of acellular EIA or ICA when compared to fresh tissues. The mean ultimate tensile strength of fresh ICA was found to be 3.90±0.64 MPa and 4.13±1.00 MPa for axial and circumferential directions respectively. The corresponding values for acellular ICA were 3.92±0.87 MPa and 4.82±0.87 MPa. The means of the rest of the biomechanical parameters are listed in Table 5. The biomechanical data indicated that the decellularisation procedure did not cause any significant changes to the tissue.

Table 5 shows biomechanical parameters from low strain rate to failure testing of fresh and acellular porcine EIA and ICA. Data is expressed as mean (n=6)±95% confidence limits.

|  | EI-E (GPa) | Coll-E (GPa) | σUTS (MPa) | Thickness (mm) |
|---|---|---|---|---|
| Fresh EIA Circumferential | | | | |
| Mean | 6.95 | 15.73 | 4.44 | 0.56 |
| 95% (C.L.) | 2.53 | 3.73 | 0.77 | 0.05 |
| Axial | | | | |
| Mean | 2.99 | 9.39 | 3.30 | 0.46 |
| 95% (C.L.) | 0.70 | 2.19 | 0.94 | 0.06 |
| Acellular EIA Circumferential | | | | |
| Mean | 6.52 | 10.94 | 4.13 | 0.55 |
| 95% (C.L.) | 2.03 | 1.36 | 1.00 | 0.08 |
| Axial | | | | |
| Mean | 2.34 | 9.05 | 2.95 | 0.48 |
| 95% (C.L.) | 0.25 | 2.3 | 1.04 | 0.07 |
| Fresh ICA Circumferential | | | | |
| Mean | 5.91 | 17.44 | 4.77 | 1.03 |
| 95% (C.L.) | 1.67 | 3.78 | 0.76 | 0.08 |
| Axial | | | | |
| Mean | 3.30 | 11.95 | 3.90 | 1.11 |
| 95% (C.L.) | 1.46 | 3.08 | 0.64 | 0.04 |
| Acellular ICA Circumferential | | | | |
| Mean | 5.36 | 13.97 | 4.82 | 1.03 |
| 95% (C.L.) | 0.46 | 3.09 | 0.87 | 0.13 |
| Axial | | | | |
| Mean | 3.12 | 12.55 | 3.92 | 1.01 |
| 95% (C.L.) | 0.71 | 2.43 | 0.87 | 0.10 |

EXAMPLE 15

Figure 20:
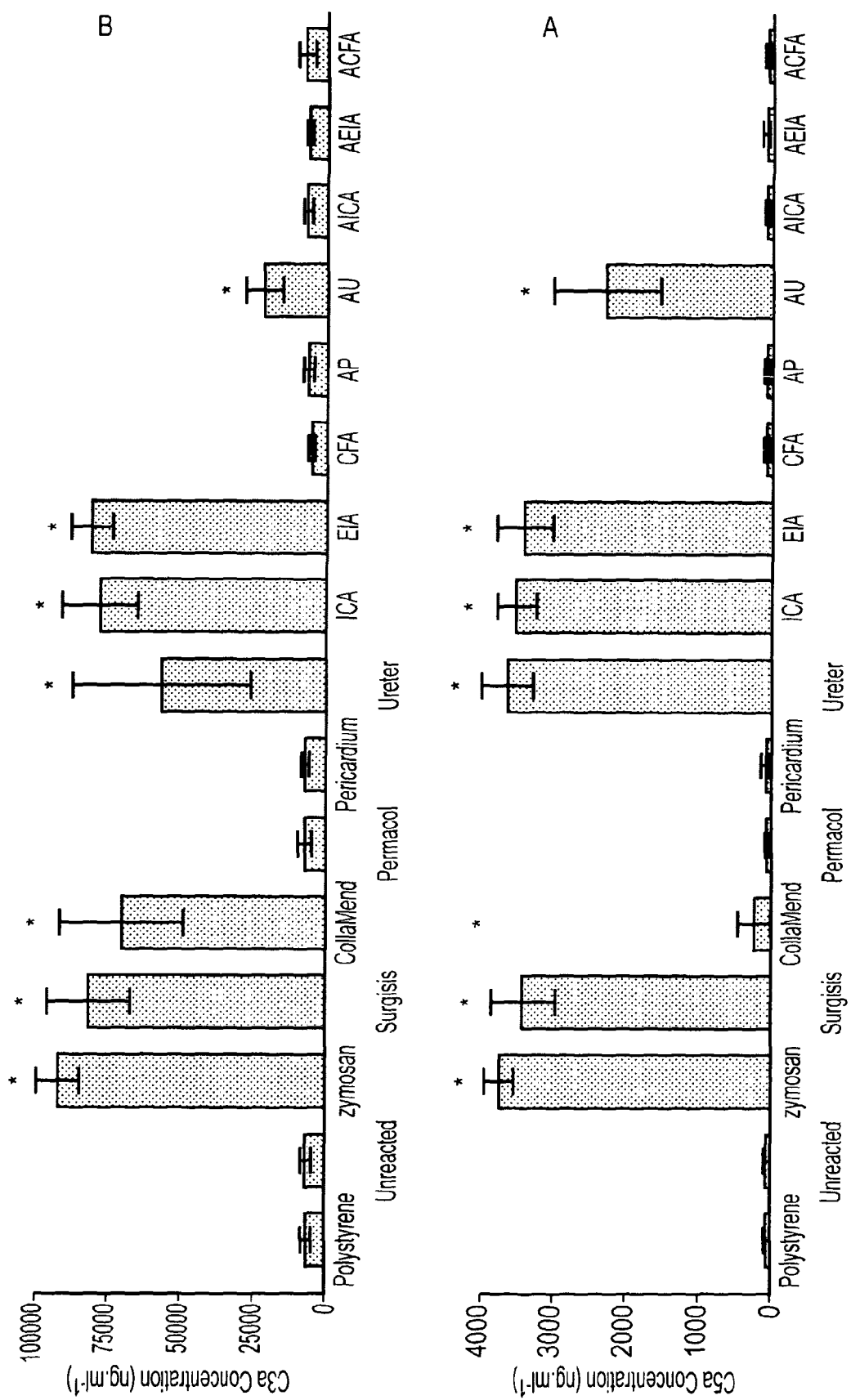
FIG. 20 shows ELISA for detection of (a) C3a or (b) C5a following reaction of normal human serum with tissue culture plastic, PBS, BSA, α-Gal BSA or Zymosan or a range of commercially available acellular biological scaffolds (Surgisis, Collamend, Permacol). Data is expressed as mean (n=6)±95% confidence limits, * represents a significant difference [compared to polystyrene] as determined by one-way ANOVA and post hoc T test. Pericardium fresh porcine pericardium; ureter, fresh porcine ureter, ICA, fresh porcine ICA EIA, fresh porcine external iliac artery AICA, acellular porcine ICA CFA, fresh human common femoral arteries AP, acellular porcine pericardium AU, acellular porcine ureter AICA, acellular porcine internal carotid artery AEIA, acellular porcine external iliac artery, ACFA acellular human common femoral artery.

Since extensive investigations have shown that the processes developed in this invention remove α-Gal as measured by immunocytochemistry and semi-quantitative ELISA, it was decided to subject the tissue to a further functional test to determine whether the acellular porcine arterial grafts will activate complement in human serum. The arterial grafts generated by the decellularisation process were compared with commercially available competitor products. Samples of each biomaterial were incubated in the presence of normal human serum for one hour at 37° C. The serum was collected and subject to ELISA to determine the presence of C3a or C5a. Initial results demonstrated that zymosan [a positive control] caused complement activation of normal human serum when compared to a PBS negative control (FIG. 20). The results demonstrated α-Gal conjugated to BSA was capable of initiating complement activation in normal human serum (FIG. 19).

The ELISA results demonstrated the production of C3a and C5a in normal human serum in response to fresh porcine tissues (FIG. 20). This was not observed with serum reacted with acellular porcine, acellular human or fresh human tissues. When human serum was reacted with Surgisis, C3a and C5a were generated. When human serum was reacted with Permacol™ or CollaMend™, no increase in C3a or C5a was observed (FIG. 21). These studies provide strong evidence that the acellular porcine scaffolds do not contain epitopes capable of reacting with pre-formed human antibodies and activating complement.

The invention claimed is:

1. A method of preparing a natural acellular vascular tissue, the method comprising obtaining a suitable donor blood vessel and subjecting it to the following methodological steps, wherein steps (iii) through (vi) are in the following order:
   (i) an incubation with 200 mM ethylenediaminetetraacetic acid (EDTA);
   (ii) a disinfection wash;
   (iii) at least two cycles of an incubation with a hypotonic buffer and an anionic detergent;
   (iv) a nuclease treatment;
   (v) a hypertonic wash; and
   (vi) a terminal sterilization process.

2. The method according to claim 1, wherein steps (i) and (ii) are performed in a reverse order.

3. The method according to claim 1, wherein the incubation with EDTA is performed in a hypertonic buffer solution.

4. The method according to claim 1, wherein the disinfection wash comprises a wash in a hypotonic buffer solution comprising vancomycin, gentamicin and polymyxin.

5. The method according to claim 1, wherein the anionic detergent is sodium dodecyl sulfate (SDS).

6. The method according to claim 1, wherein the nuclease treatment of step (iv) comprises an incubation in a nuclease solution comprising a hypotonic buffer including a DNAase and a RNAase.

7. The method according to claim 1, wherein the hypertonic incubation of step (v) comprises an incubation in a hypertonic buffer comprising TRIS and NaCl.

8. The method according to claim 1, wherein the terminal sterilization process provides viral clearance and a reduction of bioburden.

9. The method according to claim 1, wherein the terminal sterilization process is one or more processes selected from the group comprising incorporation or coating of an antimicrobial agent, treatment with a cross-linking agent, treatment with a sterilizing agent, irradiation and treatment with supercritical $CO_2$.

10. The method according to claim 1, further including a step of coating an internal and/or external surface of the natural acellular vascular tissue with a material selected from the group comprising anticoagulants, synthetic pentasaceharide inhibitors, direct thrombin inhibitors, Vitamin K antagonists, Factor Xa inhibitors, silver, collagen IV, elastin, glycoproteins, glycosaminoglycans, synthetic or natural peptides and mixtures thereof.

11. The method according to claim 1, further including a step of seeding the natural acellular vascular tissue with a single or mixed population of cells elected according to a transplant site and selected from the group comprising epithelial cells, smooth muscle cells, pluripotent and multipotent stem cells and fibroblasts.

12. The method according to claim 1, wherein porcine donor blood vessel is up to 30 cm in length and bovine donor blood vessel is up to 80 cm in length.

\* \* \* \* \*